(12) United States Patent
Omran et al.

(10) Patent No.: US 11,548,891 B1
(45) Date of Patent: Jan. 10, 2023

(54) QUATERNARY AMMONIUM SALTS OF PHENANTHROINDOLIZIDINE AND PHENANTHROQUINOLIZIDINE ALKALOIDS AS HYPOXIA-TARGETED ANTICANCER AGENTS

(71) Applicant: BATTERJEE MEDICAL COLLEGE, Jeddah (SA)

(72) Inventors: Ziad Omran, Jeddah (SA); Omeima Abdullah, Jeddah (SA); Ikhlas A. Sindi, Jeddah (SA); Ahmed Altyar, Jeddah (SA); Afnan S. Batubara, Jeddah (SA)

(73) Assignee: BATTERJEE MEDICAL COLLEGE, Jeddah (SA)

( * ) Notice: Subject to any disclaimer, the term of this patent is extended or adjusted under 35 U.S.C. 154(b) by 0 days.

(21) Appl. No.: 17/727,273

(22) Filed: Apr. 22, 2022

(51) Int. Cl.
  A61K 31/437 (2006.01)
  C07D 221/18 (2006.01)
  C07D 471/04 (2006.01)

(52) U.S. Cl.
  CPC .................................. C07D 471/04 (2013.01)

(58) Field of Classification Search
  CPC .......................... A61K 31/437; C07D 221/18
  USPC ............................................. 514/283; 546/42
  See application file for complete search history.

(56) References Cited

FOREIGN PATENT DOCUMENTS

| CN | 105130985 A | 12/2015 |
|---|---|---|
| WO | 2017/050262 A1 | 3/2017 |
| WO | WO-2021127456 A1 * | 6/2021 |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Wolff, Manfred E., Ed. Burger's Medicinal Chemistry and Drug Discovery—Fifth Edition, vol. 1: Principles and Practice, New York: John Wiley & Sons, 1994, 975-977.*
Hackam, et al. JAMA, 296(14), 2006, 1731-1732.*
Han, et al. ; Design, Synthesis, and Antitobacco Mosaic Virus Activity of Water-Soluble Chiral Quaternary Ammonium Salts of Phenanthroindolizidines Alkaloids ; Journal of Agricultural and Food Chemistry, 66, 4 ; pp. 780-788 ; Jan. 22, 2018.
Maria de Fatima Pereira, et al. ; Recent Advances in Phenanthroindolizidine and Phenanthroquinolizidine Derivatives with Anticancer Activities ; Anti-Cancer Agents in Medicinal Chemistry, 15 ; pp. 1080-1091 ; 2015.

* cited by examiner

Primary Examiner — Douglas M Willis
(74) Attorney, Agent, or Firm — Oblon, McClelland, Maier & Neustadt, L.LP.

(57) ABSTRACT

A compound having a structure of formula (I):

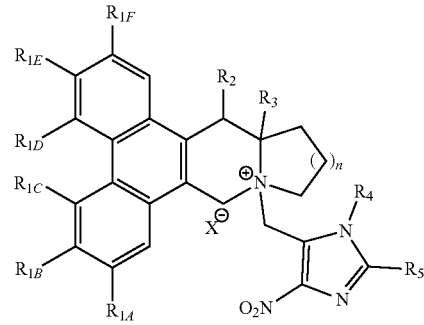

Formula (I)

Wherein each of $R_{1A}$, $R_{1B}$, $R_{1C}$, $R_{1D}$, $R_{1E}$ and $R_{1F}$ is independently selected from the group consisting of a hydrogen atom, a hydroxide group, and a substituted or unsubstituted $C_1$-$C_8$ alkoxy group, $R_2$ is selected from the group consisting of a hydrogen atom and a hydroxide group, $R_3$ is hydrogen atom, $R_4$ is selected from the group consisting of a hydrogen atom, a $C_1$-$C_3$ alkyl group, and a $C_1$-$C_3$ fluoroalkyl group, $R_5$ is selected from the group consisting of a hydrogen atom, a $C_1$-$C_6$ alkyl, and a $C_1$-$C_6$ fluoroalkyl, n is 1 or 2, and X is a negatively charged anion. Removal of the substituted nitroimidazole affords a phenanthroindolizidine or phenanthroquinolizidine alkaloid derivative. The compound is used in a pharmaceutical composition and a method of treating a proliferative disease.

20 Claims, 14 Drawing Sheets

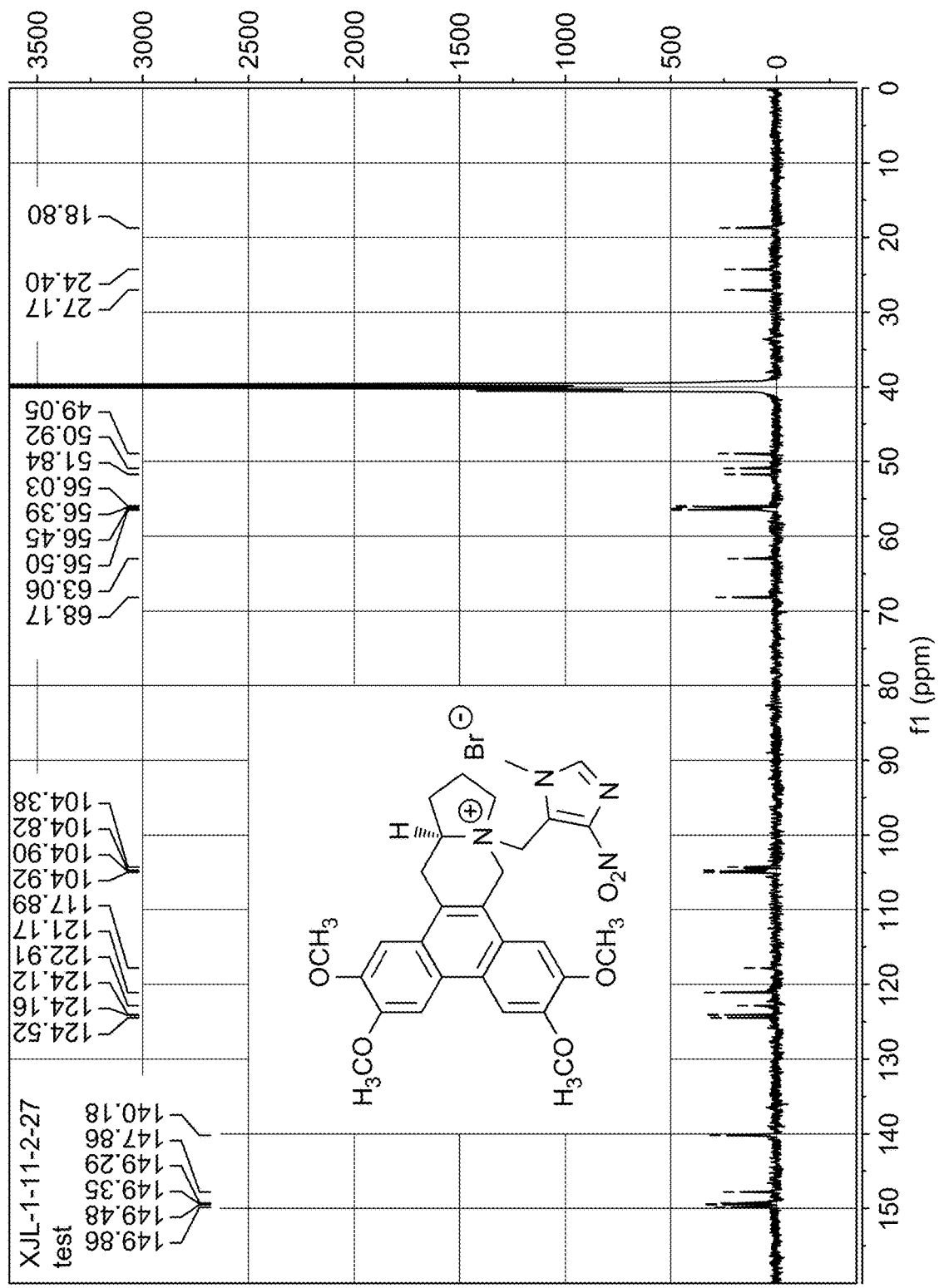

QUATERNARY AMMONIUM SALTS OF PHENANTHROINDOLIZIDINE AND PHENANTHROQUINOLIZIDINE ALKALOIDS AS HYPOXIA-TARGETED ANTICANCER AGENTS

STATEMENT OF PRIOR DISCLOSURE BY THE INVENTORS

Aspects of the present disclosure are described in the article "Design, Synthesis and In-Vitro Biological Evaluation of Antofine and Tylophorine Prodrugs as Hypoxia-Targeted Anticancer Agents" published in Molecules 2021, Vol 26, 3327, available on Jun. 1, 2021, which is incorporated herein by reference in its entirety.

STATEMENT OF ACKNOWLEDGMENT

The authors would like to acknowledge the financial support provided by King Abdulaziz City for Science and Technology (KACST), Grant No. 13-MED2515-10, and Batterjee Medical College, Grant No. B-RES-2020-0028

BACKGROUND OF THE INVENTION

Field of the Invention

The present disclosure relates to phenanthroindolizidine and phenanthroquinolizidine alkaloid derivatives which act as anti-cancer agents, compositions and medicaments containing them, and processes for the preparation and use of such inhibitors, compositions and medicaments.

Discussion of the Background

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Phenanthroindolizidines and phenanthroquinolizidines are alkaloids found in plants in the Asclepiadaceae and Lauraceae families. They show a number of biological properties which makes them of interest to the medical community, particularly anti-inflammatory activity, antifungal activity, antiviral activity, and anti-cancer activity. The mechanisms of these varied activities, and the specific biological targets associated with them, however, are not well-understood. A variety of such mechanisms have been proposed including inhibition of the nuclear factor κB (NF-κB) signaling pathway, inhibition of protein synthesis during the chain elongation stage, inhibition of protein synthesis by targeting ribosomal subunits, and inhibition of hypoxia-inducible factor 1 (HIF-1).

Further, these alkaloids typically suffer from significant drawbacks, greatly limiting their clinical use. These alkaloids show severe central nervous system toxicity and significant loss of anti-cancer activity when administered in vivo. These alkaloids are typically lipophilic, allowing crossing of the blood-brain barrier, which may be a significant factor in central nervous system toxicity.

Accordingly, the present disclosure describes compounds, specifically phenanthroindolizidine and phenanthroquinolizidine alkaloid derivatives in the form of quaternary ammonium salts, having activity as anti-cancer agents, including their prodrug forms, as well as to the application of such compounds in therapy which overcome the limitations identified above.

SUMMARY OF THE INVENTION

The present disclosure relates to a compound, having a structure of formula (I):

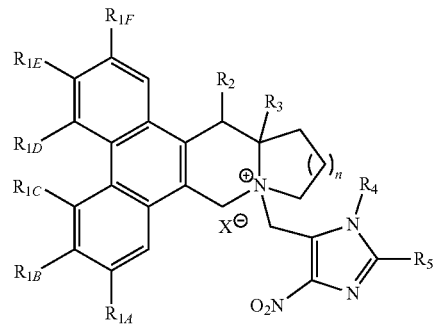

Formula (I)

or a pharmaceutically acceptable salt, solvate, stereoisomer, or prodrug thereof, wherein each of $R_{1A}$, $R_{1B}$, $R_{1C}$, $R_{1D}$, $R_{1E}$ and $R_{1F}$ is independently selected from the group consisting of a hydrogen atom, a hydroxide group, and a substituted or unsubstituted $C_1$-$C_8$ alkoxy group, $R_2$ is selected from the group consisting of a hydrogen atom and a hydroxide group, $R_3$ is hydrogen such that the carbon atom to which $R_3$ is bonded has either a (R) or (S) stereochemical configuration, $R_4$ is selected from the group consisting of a hydrogen atom, a $C_1$-$C_3$ alkyl group, and a $C_1$-$C_3$ fluoroalkyl group comprising at least one fluorine atom, $R_5$ is selected from the group consisting of a hydrogen atom, a $C_1$-$C_6$ alkyl, and a $C_1$-$C_6$ fluoroalkyl group comprising at least one fluorine atom, n is 1 or 2; and X is a negatively charged anion.

In some embodiments, the substituted or unsubstituted $C_1$-$C_8$ alkoxy group is a methoxy group.

In some embodiments, each of $R_{1B}$, $R_{1E}$ and $R_{1F}$ is a methoxy group and each of $R_{1A}$, $R_{1C}$ and $R_{1D}$ is a hydrogen atom.

In some embodiments, each of $R_{1A}$, $R_{1B}$, $R_{1E}$ and $R_{1F}$ is a methoxy group and each of $R_{1C}$ and $R_{1D}$ is a hydrogen atom.

In some embodiments, $R_4$ is a methyl group.

In some embodiments, $R_5$ is a hydrogen atom.

In some embodiments, X is selected from the group consisting of a halide, a methanesulfonate, a trifluoromethanesulfonate, an acetate, a trifluoroacetate, a tosylate, a lactate, a citrate, and a formate.

In some embodiments, X is a halide.

In some embodiments, the halide is bromide.

In some embodiments, compound is selected from the group consisting of:

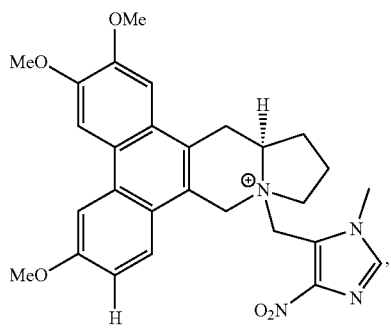

Formula (II)

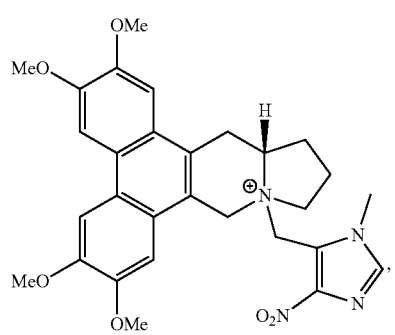

Formula (III)

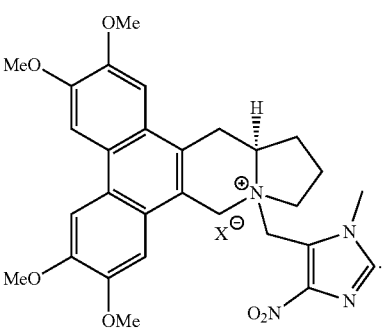

Formula (IV)

The present disclosure also relates to a pharmaceutical composition, comprising the compound and a pharmaceutically acceptable carrier and/or excipient.

In some embodiments, the pharmaceutically acceptable carrier and/or excipient is at least one selected from the group consisting of a buffer, an inorganic salt, a fatty acid, a vegetable oil, a synthetic fatty ester, a surfactant, and a polymer.

In some embodiments, the compound is at least one selected from the group consisting of:

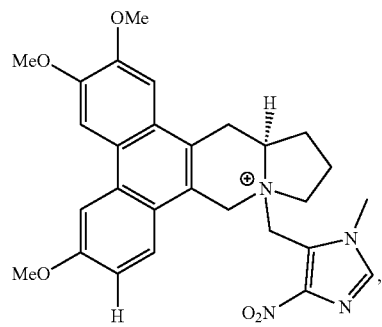

Formula (II)

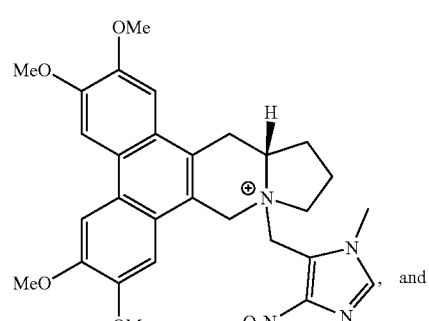

Formula (III)

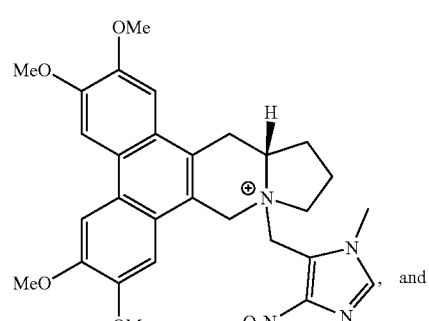

Formula (IV)

The present disclosure also relates to a method of treating a proliferative disease in an animal, the method comprising administering to the animal a therapeutically effective amount of the compound.

In some embodiments, the proliferative disease is at least one selected from the group consisting of a lung cancer, a colon/colorectal cancer, and a breast cancer.

In some embodiments, the compound is at least one selected from the group consisting of:

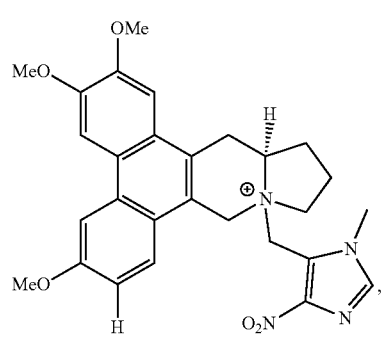

Formula (II)

-continued

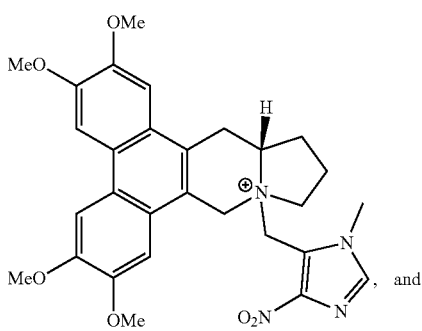

Formula (III)

, and

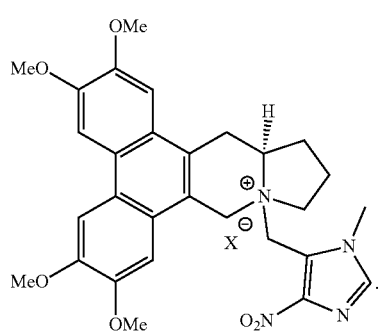

Formula (IV)

BRIEF DESCRIPTION OF THE DRAWINGS

FIG. 7A shows the $^1$H-NMR spectrum of compound 5a.
FIG. 7B shows the $^{13}$C-NMR spectrum of compound 5a.
FIG. 7C shows the ESI mass spectrum of compound 5a.
FIG. 9B shows the $^{13}$C-NMR spectrum of compound 5c.

DETAILED DESCRIPTION OF THE INVENTION

Figure 1:
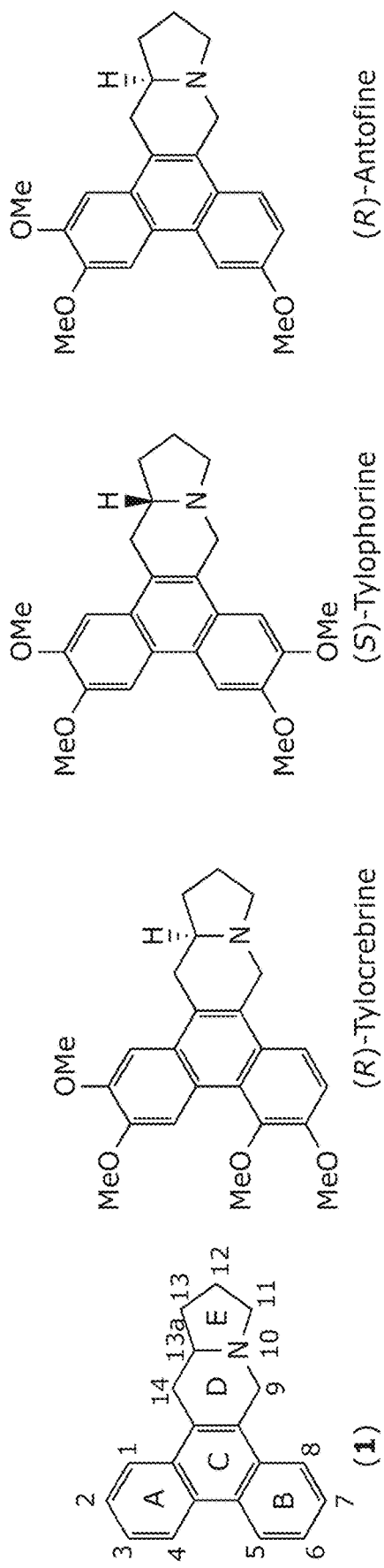
FIG. 1 shows the chemical structure of some exemplary phenanthroindolizidine alkaloids.
Figure 2:
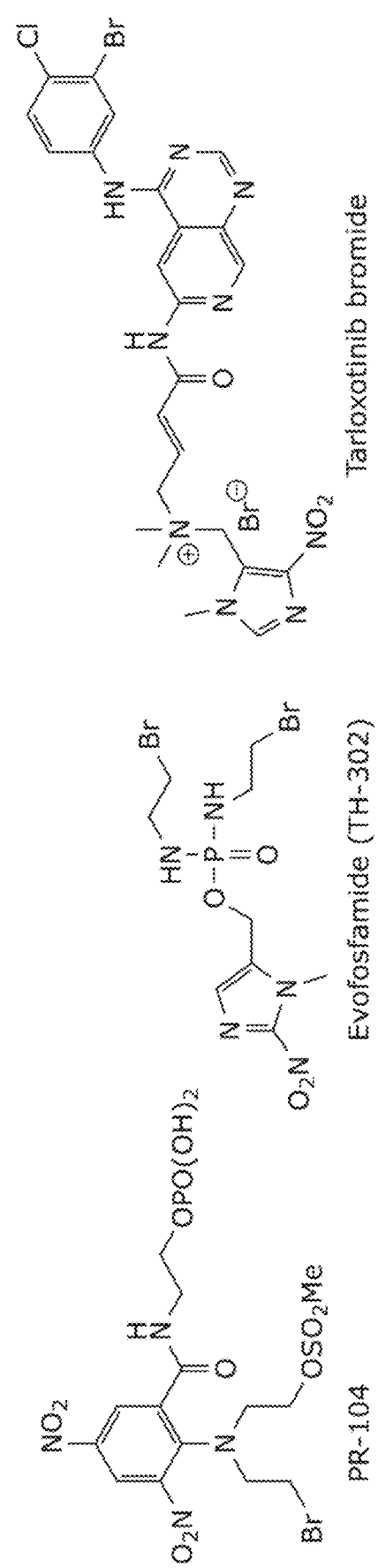
FIG. 2 shows the chemical structure of some hypoxia-targeted nitro(hetero)aromatic-based prodrugs.

In the following description, it is understood that other embodiments may be utilized and structural and operational changes may be made without departure from the scope of the present embodiments disclosed herein.

Definitions

As used herein the words "a" and "an" and the like carry the meaning of "one or more."

As used herein, the terms "optional" or "optionally" means that the subsequently described event(s) can or cannot occur or the subsequently described component(s) may or may not be present (e.g., 0 wt. %).

As used herein, the terms "compound" and "complex" are used interchangeably, and are intended to refer to a chemical entity, whether in a solid, liquid or gaseous phase, and whether in a crude mixture or purified and isolated.

As used herein, the term "solvate" refers to a physical association of a compound of this disclosure with one or more solvent molecules, whether organic or inorganic. This physical association includes hydrogen bonding. In certain instances, the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution phase and isolable solvates. Exemplary solvents include, but are not limited to, water, methanol, ethanol, n-propanol, iso-propanol, n-butanol, iso-butanol, tert-butanol, ethyl acetate and other lower alkanols, glycerine, acetone, dichloromethane (DCM), dimethyl sulfoxide (DMSO), dimethyl acetate (DMA), dimethylformamide (DMF), isopropyl ether, acetonitrile, toluene, N-methylpyrrolidone (NMP), tetrahydrofuran (THF), tetrahydropyran, other cyclic mono-, di- and tri-ethers, polyalkylene glycols (e.g. polyethylene glycol, polypropylene glycol, propylene glycol), and mixtures thereof in suitable proportions. Exemplary solvates include, but are not limited to, hydrates, ethanolates, methanolates, isopropanolates and mixtures thereof. Methods of solvation are generally known to those of ordinary skill in the art.

As used herein, the term "tautomer" refers to constitutional isomers of organic compounds that readily convert by tautomerization or tautomerism. The interconversion commonly results in the formal migration of a hydrogen atom or proton, accompanied by a switch of a single bond and adjacent double bond. Tautomerism is a special case of structural isomerism, and because of the rapid interconversion, tautomers are generally considered to be the same chemical compound. In solutions in which tautomerization is possible, a chemical equilibrium of the tautomers will be reached. The exact ratio of the tautomers depends on several factors including, but not limited to, temperature, solvent and pH. Exemplary common tautomeric pairs include, but are not limited to, ketone and enol, enamine and imine, ketene and ynol, nitroso and oxime, amide and imidic acid, lactam and lactim (an amide and imidic tautomerism in heterocyclic rings), and open-chain and cyclic forms of an acetal or hemiacetal (e.g., in reducing sugars).

As used herein, the term "stereoisomer" refers to isomeric molecules that have the same molecular formula and sequence of bonded atoms (i.e. constitution), but differ in the three-dimensional orientations of their atoms in space. This contrasts with structural isomers, which share the same molecular formula, but the bond connection of their order differs. By definition, molecules that are stereoisomers of each other represent the same structural isomer. Enantiomers are two stereoisomers that are related to each other by reflection, they are non-superimposable mirror images. Every stereogenic center in one has the opposite configuration in the other. Two compounds that are enantiomers of each other have the same physical properties, except for the direction in which they rotate polarized light and how they interact with different optical isomers of other compounds.

Diastereomers are stereoisomers not related through a reflection operation, they are not mirror images of each other. These include meso compounds, cis- and trans- (E- and Z-) isomers, and non-enantiomeric optical isomers. Diastereomers seldom have the same physical properties. In terms of the present disclosure, stereoisomers may refer to enantiomers, diastereomers, or both.

Conformers, rotamers, or conformational isomers refer to a form of isomerism that describes the phenomenon of molecules with the same structural formula but with different shapes due to rotations around one or more bonds. Different conformations can have different energies, can usually interconvert, and are very rarely isolatable. There are some molecules that can be isolated in several conformations. Atropisomers are stereoisomers resulting from hindered rotation about single bonds where the steric strain barrier to rotation is high enough to allow for the isolation of the conformers. It should be understood that all conformers, rotamers, or conformational isomer forms, insofar as they may exist, are included within the present disclosure.

In terms of the present disclosure, stereoisomers of the ring systems, stereogenic centers, and the like can all be present in the compounds, and all such stable isomers are contemplated in the present disclosure. S- and R- (or L- and D-) stereoisomers of the compounds of the present disclosure are described and may be isolated as a mixture of isomers or as separated isomeric forms. All processes or methods used to prepare compounds of the present disclosure and intermediates made therein are considered to be part of the present disclosure. When stereoisomeric products are prepared, they may be separated by conventional methods, for example, by chromatography, fractional crystallization, or use of a chiral agent.

As used herein, the term "substituted" refers to at least one hydrogen atom that is replaced with a non-hydrogen group, provided that normal valencies are maintained and that the substitution results in a stable compound. When a substituent is noted as "optionally substituted", the substituents are selected from halo, hydroxyl, alkoxy, oxo, alkanoyl, aryloxy, alkanoyloxy, amino, alkylamino, arylamino, arylalkylamino, disubstituted amines (e.g. in which the two amino substituents are selected from the exemplary group including, but not limited to, alkyl, aryl or arylalkyl), alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, aryalkylthiono, alkylsulfonyl, arylsulfonyl, arylalkylsulfonyl, sulfonamide (e.g. —SO$_2$NH$_2$), substituted sulfonamide, nitro, cyano, carboxy, unsubstituted amide (i.e. —CONH$_2$), substituted amide (e.g. —CONHalkyl, —CONHaryl, —CONHarylalkyl or cases where there are two substituents on one nitrogen from alkyl, aryl, or alkylalkyl), alkoxycarbonyl, aryl, substituted aryl, guanidine, heterocyclyl (e.g. indolyl, imidazoyl, furyl, thienyl, thiazolyl, pyrrolidyl, pyridyl, pyrimidiyl, pyrrolidinyl, piperidinyl, morpholinyl, piperazinyl, homopiperazinyl and the like), substituted heterocyclyl and mixtures thereof. The substituents may themselves be optionally substituted, and may be either unprotected, or protected as necessary, as known to those of ordinary skill in the art, for example, as taught in Greene, et al., "Protective Groups in Organic Synthesis", John Wiley and Sons, Second Edition, 1991, hereby incorporated by reference in its entirety.

The present disclosure is intended to include all isotopes of atoms occurring in the present compounds. Isotopes include those atoms having the same atomic number but different mass numbers. By way of general example, and without limitation, isotopes of hydrogen include deuterium and tritium, and isotopes of carbon include $^{13}$C and $^{14}$C. Isotopically labeled compounds of the disclosure can generally be prepared by conventional techniques known to those skilled in the art or by processes and methods analogous to those described herein, using an appropriate isotopically labeled reagent in place of the non-labeled reagent otherwise employed.

As used herein, the term "alkyl" refers to a fully saturated branched, or unbranched hydrocarbon fragment, preferably for substitution at R1 and/or R2 of Formula (I) a C$_1$-C$_6$ alkyl. Representative examples of such alkyl include, but are not limited to, methyl, ethyl, n-propyl, isopropyl, n-butyl, sec-butyl, iso-butyl, tert-butyl, n-pentyl, isopentyl, neopentyl, n-hexyl, isohexyl, 3-methylhexyl, 2,2-dimethylpentyl, 2,3-dimethylpentyl, n-heptyl, n-octyl, n-nonyl, n-decyl and the like.

The term "aryl", as used herein, includes aromatic monocyclic or multicyclic (e.g., tricyclic, bicyclic), hydrocarbon ring systems comprising or consisting of hydrogen and carbon atoms, where the ring systems may be partially saturated. Aryl groups include, but are not limited to, phenyl, tolyl, xylyl, biphenyl, naphthyl, anthracenyl, phenanthryl and tetralin. This term also includes substituted aryl and heteroaryl groups such as phenol, aryl halides or imidazyl preferably an C$_6$-C$_{10}$ aryl is chosen for substitution at R1 and R2 of Formula (I).

The term "halogen", as used herein, means fluoro, chloro, bromo and iodo.

The term "anion" means a negatively charged ion including, but not limited to, halides, such as fluoride, chloride, bromide, and iodide, nitrate, sulfate, phosphate, methanesulfonate, ethanesulfonate, p-toluenesulfonate, salicylate, malate, maleate, succinate, tartrate, citrate, acetate, perchlorate, trifluoromethanesulfonate, acetylacetonate, tetrafluoroborate, hexafluorophosphate, and hexafluoroacetylacetonate.

According to a first aspect, the present disclosure relates to a compound, having a structure of formula (I):

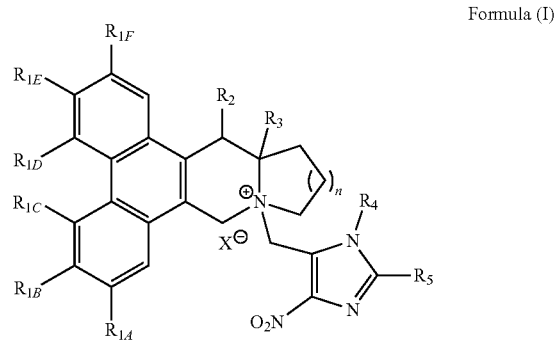

Formula (I)

or a pharmaceutically acceptable salt, solvate, stereoisomer, or prodrug thereof, wherein:

each of R$_{1A}$, R$_{1B}$, R$_{1C}$, R$_{1D}$, R$_{1E}$ and R$_{1F}$ is independently selected from the group consisting of a hydrogen atom, a hydroxide group, and a substituted or unsubstituted C$_1$-C$_8$ alkoxy group;

R$_2$ is selected from the group consisting of a hydrogen atom and a hydroxide group;

R$_3$ is hydrogen such that the carbon atom to which R$_3$ is bonded has either a (R) or (S) stereochemical configuration;

$R_4$ is selected from the group consisting of a hydrogen atom, a $C_1$-$C_3$ alkyl group, and a $C_1$-$C_3$ fluoroalkyl group comprising at least one fluorine atom.

$R_5$ is selected from the group consisting of a hydrogen atom, a $C_1$-$C_6$ alkyl, and a $C_1$-$C_6$ fluoroalkyl group comprising at least one fluorine atom.

n is 1 or 2; and

X is a negatively charged anion.

In some embodiments, the substituted or unsubstituted $C_1$-$C_8$ alkoxy group is a methoxy group. In some embodiments, each of $R_{1B}$, $R_{1E}$ and $R_{1F}$ is a methoxy group and each of $R_{1A}$, $R_{1C}$, and $R_{1D}$ is a hydrogen atom. In some embodiments, each of $R_{1A}$, $R_{1B}$, $R_{1E}$ and $R_{1F}$ is a methoxy group and each of $R_{1C}$ and $R_{1D}$ is a hydrogen atom. In some embodiments, $R_4$ is a methyl group. In some embodiments, $R_5$ is a hydrogen atom.

In some embodiments, X is selected from the group consisting of a halide, a methanesulfonate, a trifluoromethanesulfonate, an acetate, a trifluoroacetate, a tosylate, a lactate, a citrate, and a formate. In some embodiments, X is a halide. In preferred embodiments, the halide is bromide.

In some preferred embodiments, the compound is at least one selected from the group consisting of:

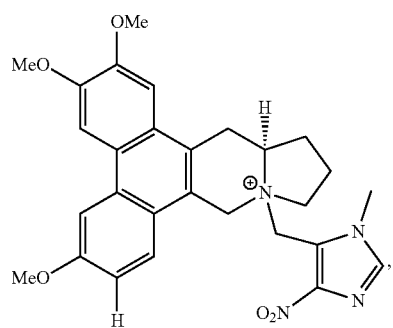

Formula (II)

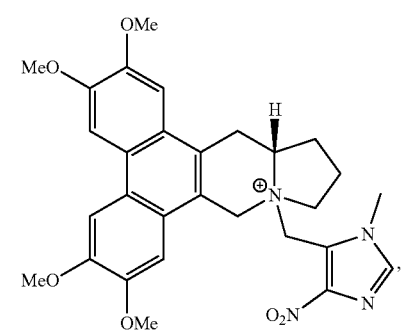

Formula (III) and

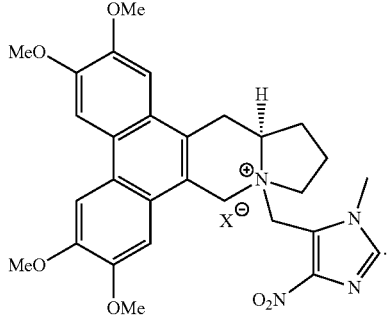

Formula (IV)

In one embodiment, the compounds of the invention comprise an anti-cancer agent core, preferably a phenanthroindolizidine or phenanthroquinolizidine anti-cancer agent core, and an aromatic nitroimidazole (or substituted nitroimidazole) substituent (herein after "nitroimidazole" or "nitroimidazole group"). The nitroimidazole may be removed by a reduction reaction (the nitroimidazole may be referred to as a "reductive trigger"). Such removal may involve breaking of the C—N bond between the quaternary ammonium nitrogen atom and the carbon of the methylene group which connects the nitroimidazole substituent to the anti-cancer agent core. The compound carries a positive charge. The positive charge of the compound has important benefits, particularly in the treatment of cancer, as will be described below.

The reduction reaction which serves to remove the nitroimidazole may be performed by or with the aid of enzymes, radiation-induced radicals, or chemical reducing agents. Radiation can, for example, be particularly effective in removing the nitroimidazole and liberating the anti-cancer agent core, thereby targeting the release of the anti-cancer agent core to regions where the radiation is provided, such as a tumor. However, it is presently preferred that the removal of the nitroimidazole group be performed by endogenous enzyme(s) present within tumors such that reduction is suppressed in the presence of oxygen, such as one-electron reductases. This preferred removal by one-electron reductases effectively targets the release of the anti-cancer agent core to regions of hypoxia within tumors. In this form, the compounds may therefore be considered prodrugs which, upon removal of the nitroimidazole unit via reduction in a tumor-associated environment (also referred to herein as "reductive activation"), release an anti-cancer agent core to produce an anti-cancer effect.

The anti-cancer agent core can be a portion or derivative of the compound of Formula (I) from which the aromatic nitroimidazole moiety has been removed. Examples of such anti-cancer agent cores include phenanthroindolizidine and phenanthroquinolizidine alkaloid derivatives, such as Antofine and Tylophorine. In some embodiments, the compound of Formula (I) therefore acts as a prodrug of Antofine and/or Tylophorine. Removal of the aromatic nitroimidazole moiety under reductive conditions releases the active anti-cancer agent core, with the nitrogen to which the trigger was linked remaining part of the released anti-cancer agent core.

For activation by endogenous reductases, the requirement that removal of the aromatic nitroimidazole moiety be effectively suppressed by oxygen is preferable. Removal of the aromatic nitroimidazole substituent may occur at the one-electron reduction level by endogenous one-electron reductases. Suppression of effective removal by oxygen may occur, for example, through reoxidation of the one-electron radical by oxygen, or by oxidation by reducing intermediates required for prodrug reduction. The latter would include, for example, scavenging by oxygen of radiation-induced reducing radicals such as the aquated electron, or oxidation of reducing intermediates in the catalytic cycle of reductase enzymes. But whatever the mechanism, an oxygen-suppressive effect is the result.

Such suppression may be advantageous for the selective targeting of the compounds. Tumor-associated environments will commonly be hypoxic. Without wishing to be bound by theory, restriction of inhibitor release to hypoxic tissue and subsequent back-diffusion of the inhibitor to oxygenated areas of the tumor is believed to be a primary basis for tumor selectivity via endogenous enzymes.

According to a further aspect, the present disclosure relates to a pharmaceutical composition containing the compound of formula (I) of the first aspect and a pharmaceutically acceptable carrier and/or excipient.

As used herein, a "composition" or a "pharmaceutical composition" refers to a mixture of the active ingredient with other chemical components, such as pharmaceutically acceptable carriers and excipients. One purpose of a composition is to facilitate administration of the compound disclosed herein in any of its embodiments to a subject. Pharmaceutical compositions of the present disclosure may be manufactured by processes well known in the art, e.g., by means of conventional mixing, dissolving, granulating, dragee-making, levigating, emulsifying, encapsulating, entrapping or lyophilizing processes. Depending on the intended mode of administration (oral, parenteral, or topical), the composition can be in the form of solid, semi-solid or liquid dosage forms, such as tablets, suppositories, pills, capsules, powders, liquids, or suspensions, preferably in unit dosage form suitable for single administration of a precise dosage.

The term "active ingredient", as used herein, refers to an ingredient in the composition that is biologically active, for example, one or more of the compound represented by formula (I), solvates thereof, tautomers thereof, stereoisomers thereof, or any mixtures thereof. In some embodiments, other active ingredients in addition to the complexes of the current disclosure may be incorporated into a pharmaceutical composition, for example, a second active ingredient which is chemically distinct from the compound.

In one or more embodiments, the compound of formula (I) of the pharmaceutical composition is selected from the group consisting of

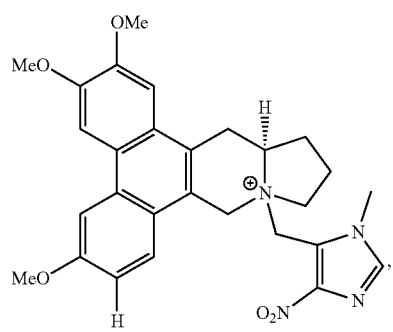

Formula (II)

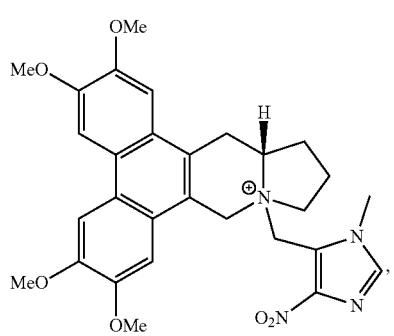

Formula (III)

and

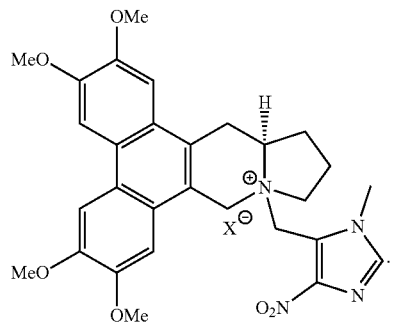

Formula (IV)

When the compounds are administered as pharmaceuticals, to humans and animals, they can be given per se or as a pharmaceutical composition containing the active ingredient(s) in combination with a pharmaceutically acceptable carrier and/or excipient. The pharmaceutical composition may contain at least 0.0001 wt. %, at least 0.001 wt. %, at least 0.01 wt. %, at least 0.05 wt. %, at least 0.1 wt. %, at least 0.5 wt. %, at least 5 wt. %, at least 10 wt. %, at least 15 wt. %, at least 20 wt. %, at least 25 wt. %, at least 30 wt. %, at least 35 wt. %, at least 40 wt. %, at least 45 wt. %, at least 50 wt. %, at least 55 wt. %, at least 60 wt. %, at least 65 wt. %, at least 70 wt. %, at least 75 wt. %, at least 80 wt. %, at least 85 wt. %, at least 90 wt. %, at least 95 wt. %, at least 99 wt. %, or at least 99.9 wt. % of the compound of formula (I) relative to a total weight of the pharmaceutical composition. For example, when formulated as a solution, the pharmaceutical composition may contain 0.1-10,000 µM of the compound of formula (I) relative to a total volume of the pharmaceutical composition, preferably 0.5-5,000 µM, preferably 1-4,500 µM, preferably 2-4,000 µM, preferably 3-3,500 µM, preferably 4-3,000 µM, preferably 5-2,500 µM, preferably 6-2,000 µM, preferably 7-1,500 µM, preferably 8-1,250 µM, preferably 10-1,100 µM of the compound relative to a total volume of the pharmaceutical composition.

In some embodiments, the active ingredient of the current disclosure, e.g. the compound of formula (I), a solvate thereof, a tautomer thereof, a stereoisomer thereof, prodrug thereof, or any mixtures thereof, provides utility as an anticancer agent in reducing the viability of cancer cells derived from human cancer cell lines including, but not limited to, lung cancer cell lines (e.g., A549, NCI-H460, SHP-77, COR-L23/R, NCI-H69/LX20); cervical cancer cell lines (e.g., HeLa, ME-180, R-ME-180); liver cancer cell lines (e.g., HepG2, PLC/PRF/5, THLE-3, C3A, SNU-182, SNU-398, SNU-387, SNU-423, SNU-475, SNU-449, and Hep 3B2.1-7); ovarian cancer cell lines (e.g., NCI-ADR/RES, OVCAR-03, A2780, A2780cis, OV7, PEO23); breast cancer cell lines (e.g., MDA-MB-231, MCF-7, SK-BR-3, T47D, VP303); stomach cancer cell lines (e.g., N87, SNU-16, SNU-5, SNU-1, KATO III, AGS); colon/colorectal cancer cell lines (e.g., HCT-116, RKO, SW480, CACO-2, HT-29, HCT15, MDST8, GP5d, DLD1, SW620, SW403, T84); prostate cancer cell lines (e.g., DU145, PC-3); brain tumor cell lines (e.g., U251); renal cancer cell lines (e.g., 786-0); skin cancer or melanoma cell lines (e.g., UACC-62, C32TG, A375, MCC26); and bone cancers such as osteosarcoma cell lines (e.g., MG-63). Preferably, the active ingredient of the current disclosure, e.g. the compound of formula (I), a solvate thereof, a tautomer thereof, a stereoisomer thereof, prodrug thereof, or any mixtures thereof, provides utility as an anticancer agent in reducing the viability of cancer cells derived from lung cancer cell lines (e.g., A549, NCI-H460, SHP-77, COR-L23/R, NCI-H69/LX20), breast cancer cell lines (e.g., MDA-MB-231, MCF-7, SK-BR-3, T47D, VP303), and colon/colorectal cancer cell lines (e.g., HCT-116, RKO, SW480, CACO-2, HT-29, HCT15, MDST8, GP5d, DLD1, SW620, SW403, T84).

In some embodiments, the cancer cells are collected from a human patient who is at risk of having, is suspected of having, has been diagnosed with, or is being monitored for recurrence of at least one type of cancer, preferably lung cancer, breast cancer, and/or colon/colorectal cancer.

In some embodiments, the active ingredient of the present disclosure, e.g., the compound of formula (I), a solvate thereof, a tautomer thereof, a stereoisomer thereof, prodrug thereof, or any mixtures thereof, may provide utility as an anticancer agent in reducing viability of cancer cells derived from human cancer cell lines which are resistant to, or which are susceptible to becoming resistant to, other therapeutic agents/chemotherapy agents such as platinum-based chemotherapy drugs including, but not limited to, cisplatin, carboplatin, and oxaliplatin. In at least one embodiment, the cancer cells are cisplatin-resistant cancer cells. These cells may be generated by culturing cancer cells with low doses of cisplatin in order to build their resistance to cisplatin while maintaining cell viability. Examples of cisplatin-resistant cancer cells include, but are not limited to, cisplatin resistant cervical cancers (e.g., R-ME-180), A549 cisplatin-resistant lung cancer cells, MCF-7 cisplatin-resistant breast cancer cells, A2780cis cisplatin-resistant ovarian cancer cells, and SGC7901cis cisplatin-resistant gastrointestinal cancer cells.

In some embodiments, the ability of the active ingredient to reduce the viability of cancer cells may be determined by contacting the pharmaceutical composition with the cancer cells and then performing cell viability assays. Methods of such assays include, but are not limited to, sulforhodamine-B (SRB) assay, ATP test, Calcein AM assay, clonogenic assay, ethidium homodimer assay, Evans blue assay, 2',7'-dichlorofluorescin diacetate (DCFDA) or 2',7'-dichlorodihydrofluorescein diacetate (H2DCFDA) staining assay, fluorescein diacetate hydrolysis/propidium iodide staining assay, annexin V/fluorescein isothiocyanate (FITC)/propidium iodide staining assay, flow cytometry, Formazan-based assays (MTT, XTT), green fluorescent protein assay, lactate dehydrogenase (LDH) assay, methyl violet assay, propidium iodide assay, Resazurin assay, trypan blue assay, 4',6'-diamidino-2-phenylindole (DAPI) assay, TUNEL assay, a fluorochrome-labeled inhibitors of caspases (FLICA)-based assay, primary (1°) colonosphere formation assay, thioredoxin reductase assay, 20S proteasome activity assay, and in vitro scratch assay (for cell migration analysis). In a preferred embodiment, the cell viability assay is performed via ATP test using CellTiter-Glo® Luminescent Cell Viability Assay, available from Promega, Madison, Wis., USA.

As used herein, the term "cytotoxic effective amount" refers to a concentration of the active ingredient that reduces the viability of the cancer cells by at least 5%, at least 10%, at least 15%, at least 20%, at least 30%, at least 40%, at least 50%, at least 60%, at least 70%, at least 80% or at least 90%, relative to cancer cells not treated with the active ingredient. The reduction in viability may occur no more than 10 days, no more than 7 days, no more than 5 days, no more than 3 days, or no more than 2 days after the active ingredient is contacted with the cancer cells. In one embodiment, the cytotoxic effective amount may be the $IC_{50}$ which is a concentration of an active ingredient which causes the death of 50% of cellular population of the cancer cells in 6-96 hours, 12-72 hours, or 24-48 hours.

In one embodiment, the $IC_{50}$ of the presently disclosed compounds, the solvate thereof, the tautomer thereof, the stereoisomer thereof, prodrug thereof, or mixtures thereof against lung cancer cells (e.g. H460) is in a range 10,000-100,000 nM, preferably 12,500 to 90,000 nM, preferably 15,000 to 80,000 nM under normoxic conditions. In one embodiment, the $IC_{50}$ of the presently disclosed compounds, the solvate thereof, the tautomer thereof, the stereoisomer thereof, prodrug thereof, or mixtures thereof against lung cancer cells (e.g. H460) is in a range of 100 to 10,000 nM, preferably 250 to 7,500 nM, preferably 500 to 6,500 nM under hypoxic conditions.

In another embodiment, the $IC_{50}$ of the presently disclosed compounds, the solvate thereof, the tautomer thereof, the stereoisomer thereof, prodrug thereof, or mixtures thereof against colon/colorectal cancer cells (e.g. HCT116) is in a range of 2,500 to 25,000 nM, preferably 3,000 to 20,000 nM, preferably 4,000 to 17,500 nM, under normoxic conditions. In another embodiment, the $IC_{50}$ of the presently disclosed compounds, the solvate thereof, the tautomer thereof, the stereoisomer thereof, prodrug thereof, or mixtures thereof against colon/colorectal cancer cells (e.g. HCT116) is in a range of 100 to 5,000 nM, preferably 250 to 4,000 nM, preferably 400 to 3250 nM under hypoxic conditions.

As used herein "hypoxic conditions" refer to conditions of cellular growth and/or physiological tissues in which the oxygen concentration is lower than the oxygenation of the respective normal tissues. Typically, hypoxic conditions refer to conditions in which an average oxygen concentration is 1%-2% $O_2$ and below. This is contrasted with "normoxic conditions", which refers to conditions of cellular growth and/or physiological tissues in which the oxygen concentration is at the respective normal tissue concentration, typically 4% to 10% $O_2$ depending on the tissue or normal laboratory cell growth conditions of ~20% $O_2$.

In some embodiments, other active ingredients in addition to the compounds of the current disclosure may be incorporated into the pharmaceutical composition. In one embodiment, the pharmaceutical composition includes an additional active ingredient that is chemically distinct from the compound of formula (I), such as a chemotherapeutic agent or an anticancer agent, for the treatment or prevention of neoplasm, of tumor or cancer cell division, growth, proliferation and/or metastasis in the subject; induction of death or apoptosis of tumor and/or cancer cells; and/or any other forms of proliferative disorder.

The additional active ingredient may be an anticancer agent and may include, but is not limited to, at least one of a mitotic inhibitor; an alkylating agent; an antimetabolite; a cell cycle inhibitor; an enzyme; a topoisomerase inhibitor; a biological response modifier; an anti-hormone; a tubulin inhibitor; a tyrosine-kinase inhibitor; an antiangiogenic agent such as MMP-2, MMP-9 and COX-2 inhibitor; an anti-androgen; a platinum coordination complex (cisplatin, oxaliplatin, carboplatin); a substituted urea such as hydroxyurea; a methylhydrazine derivative; an adrenocortical suppressant, e.g., mitotane, aminoglutethimide; a hormone and/or hormone antagonist such as the adrenocorticosteriods (e.g., prednisone), progestins (e.g., hydroxyprogesterone caproate), an estrogen (e.g., diethylstilbestrol); an antiestrogen such as tamoxifen; androgen, e.g., testosterone propionate; and an aromatase inhibitor, such as anastrozole, and AROMASIN (exemestane).

Exemplary anticancer agents include, but are not limited to, tubulin binding agents including paclitaxel, epothilone, docetaxel, discodermolide, etoposide, vinblastine, vincristine, teniposide, vinorelbine, and vindesine; tyrosine-kinase inhibitors including imatinib, nilotinib, dasatinib, bosutinib, ponatinib, and bafetinib; alkylating antineoplastic agents including busulfan, carmustine, chlorambucil, cyclophosphamide, cyclophosphamide, dacarbazine, ifosfamide, lomustine, mechlorethamine, melphalan, mercaptopurine, procarbazine; antimetabolites including cladribine, cytarabine, fludarabine, gemcitabine, pentostatin, 5-fluorouracil, clofarabine, capecitabine, methotrexate, thioguanine; cytotoxic antibiotics including daunorubicin, doxorubicin, idarubicin, mitomycin, actinomycin, epirubicin; topoisomerase inhibitors including irinotecan, mitoxantrone, topotecan, and mixtures thereof.

As used herein, other non-cancerous proliferative disorders that may also be treated by the currently disclosed pharmaceutical composition include, but are not limited to, atherosclerosis, rheumatoid arthritis, psoriasis, idiopathic pulmonary fibrosis, scleroderma, cirrhosis of the liver, lymphoproliferative disorder, other disorders characterized by epidermal cell proliferation such as verruca (warts), and dermatitis. The active ingredient of the current disclosure may also exhibit other therapeutic activities such as antimicrobial (e.g. antibacterial, antifungal, antiviral, antimycobacterial), antimalarial, pesticidal, antioxidant, as well as anti-inflammatory efficacies.

As used herein, a "pharmaceutically acceptable carrier" refers to a carrier or diluent that does not cause significant irritation to an organism, does not abrogate the biological activity and properties of the administered active ingredient, and/or does not interact in a deleterious manner with the other components of the composition in which it is contained. The term "carrier" encompasses any excipient, binder, diluent, filler, salt, buffer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g. Remington's Pharmaceutical Sciences, 21st Edition, ed. University of the Sciences in Philadelphia, Lippincott, Williams & Wilkins, Philadelphia Pa., 2005, which is incorporated herein by reference in its entirety). Some examples of physiologically acceptable carriers include antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.). An "excipient" refers to an inert substance added to a composition to further facilitate administration of a compound. Examples, without limitation, of excipients include calcium carbonate, calcium phosphate, various sugars and types of starch, cellulose derivatives, gelatin, vegetable oils, and polyethylene glycols.

In one or more embodiments, the pharmaceutical composition contains 0.1 to 99.9999 wt. %, preferably 1 to 99.999 wt. %, preferably 5 to 99.99 wt. %, preferably 10 to 99.9 wt. %, preferably 15 to 99 wt. %, preferably 20 to 90 wt. %, preferably 30 to 85 wt. %, preferably 40 to 80 wt. %, preferably 50 to 75 wt. %, preferably 60 to 70 wt. % of the pharmaceutically acceptable carrier and/or excipient relative to a total weight of the pharmaceutical composition.

In one or more embodiments, the pharmaceutically acceptable carrier and/or excipient is at least one selected from the group consisting of a buffer, an inorganic salt, a fatty acid, a vegetable oil, a synthetic fatty ester, a surfactant, and a polymer.

Exemplary buffers include, but are not limited to, phosphate buffers, citrate buffer, acetate buffers, borate buffers, carbonate buffers, bicarbonate buffers, and buffers with other organic acids and salts.

Exemplary inorganic salts include, but are not limited to, calcium carbonate, calcium phosphate, disodium hydrogen phosphate, potassium hydrogen phosphate, sodium chloride, zinc oxide, zinc sulfate, and magnesium trisilicate.

Exemplary fatty acids include, but are not limited to, an omega-3 fatty acid (e.g., linolenic acid, docosahexaenoic acid, eicosapentaenoic acid) and an omega-6 fatty acid (e.g., linoleic acid, eicosadienoic acid, arachidonic acid). Other fatty acids, such as oleic acid, palmitoleic acid, palmitic acid, stearic acid, and myristic acid, may be included.

Exemplary vegetable oils include, but are not limited to, avocado oil, olive oil, palm oil, coconut oil, rapeseed oil, soybean oil, corn oil, sunflower oil, cottonseed oil, and peanut oil, grape seed oil, hazelnut oil, linseed oil, rice bran oil, safflower oil, sesame oil, brazil nut oil, carapa oil, passion fruit oil, and cocoa butter.

Exemplary synthetic fatty esters include, without limitation, methyl, ethyl, isopropyl and butyl esters of fatty acids (e.g., isopropyl palmitate, glyceryl stearate, ethyl oleate, isopropyl myristate, isopropyl isostearate, diisopropyl sebacate, ethyl stearate, di-n-butyl adipate, dipropylene glycol pelargonate), $C_{12}$-$C_{16}$ fatty alcohol lactates (e.g., cetyl lactate and lauryl lactate), propylene dipelargonate, 2-ethylhexyl isononoate, 2-ethylhexyl stearate, isopropyl lanolate, 2-ethylhexyl salicylate, cetyl myristate, oleyl myristate, oleyl stearate, oleyl oleate, hexyl laurate, isohexyl laurate, propylene glycol fatty ester, and polyoxyethylene sorbitan fatty ester. As used herein, the term "propylene glycol fatty ester" refers to a monoether or diester, or mixtures thereof, formed between propylene glycol or polypropylene glycol and a fatty acid. The term "polyoxyethylene sorbitan fatty ester" denotes oleate esters of sorbitol and its anhydrides, typically copolymerized with ethylene oxide.

Surfactants may act as detergents, wetting agents, emulsifiers, foaming agents, and dispersants. Surfactants that may be present in the compositions of the present disclosure include zwitterionic (amphoteric) surfactants, e.g., phosphatidylcholine, and 3-[(3-cholamidopropyl)dimethylammonio]-1-propanesulfonate (CHAPS), anionic surfactants, e.g., sodium lauryl sulfate, sodium octane sulfonate, sodium decane sulfonate, and sodium dodecane sulfonate, non-ionic surfactants, e.g., sorbitan monolaurate, sorbitan monopalmitate, sorbitan trioleate, polysorbates such as polysorbate 20 (Tween 20), polysorbate 60 (Tween 60), and polysorbate 80 (Tween 80), cationic surfactants, e.g., decyltrimethylammonium bromide, dodecyltrimethylammonium bromide, tetradecyltrimethylammonium bromide, tetradecyltrimethylammonium chloride, and dodecylammonium chloride, and combinations thereof.

Exemplary polymers include, without limitation, polylactides, polyglycolides, polycaprolactones, polyanhydrides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(maleic anhydride), a polyvinyl alcohols, and copolymers, terpolymers, or combinations or mixtures therein. The copolymer/terpolymer may be a random copolymer/terpolymer, or a block copolymer/terpolymer.

Depending on the route of administration e.g. oral, parental, or topical, the pharmaceutical composition may be in the form of solid dosage form such as tablets, caplets, capsules, powders, and granules, semi-solid dosage form such as ointments, creams, lotions, gels, pastes, and suppositories, liquid dosage forms such as solutions, and dispersions, inhalation dosage form such as aerosols, and spray, or transdermal dosage form such as patches.

Solid dosage forms for oral administration can include capsules, tablets, pills, powders, and granules. In such solid dosage forms, the active ingredient is ordinarily combined with one or more adjuvants appropriate to the indicated route of administration. If administered per os, the active ingredient can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering ingredients such as sodium citrate, magnesium or calcium carbonate or bicarbonate. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting ingredients, emulsifying and suspending ingredients, and sweetening, flavouring, and perfuming ingredients.

For therapeutic purposes, formulations for parenteral administration can be in the form of aqueous or non-aqueous isotonic sterile injection solutions or suspensions. The term "parenteral", as used herein, includes intravenous, intravesical, intraperitoneal, subcutaneous, intramuscular, intralesional, intracranial, intrapulmonal, intracardial, intrasternal, and sublingual injections, or infusion techniques. These solutions and suspensions can be prepared from sterile powders or granules having one or more of the carriers or diluents mentioned for use in the formulations for oral administration.

The active ingredient(s) can be dissolved in aqueous or non-aqueous carriers including, but not limited to, water, ethanol, benzyl alcohol, DMSO, polyethylene glycol, propylene glycol, ethanol, corn oil, cottonseed oil, peanut oil, sesame oil, sodium chloride, and/or various buffers. Other adjuvants and modes of administration are well and widely known in the pharmaceutical art.

Injectable preparations, for example, sterile injectable aqueous or oleaginous suspensions can be formulated according to the known art using suitable dispersing or wetting ingredients and suspending ingredients. The sterile injectable preparation can also be a sterile injectable solution or suspension in a non-toxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids, such as oleic acid, find use in the preparation of injectables. Dimethyl acetamide, surfactants including ionic and non-ionic detergents, polyethylene glycols can be used. Mixtures of solvents and wetting ingredients such as those discussed above are also useful.

Formulations of the pharmaceutical compositions of the disclosure for rectal or vaginal administration may be presented as a suppository, which may be prepared by mixing one or more compounds of Formula (I) with one or more suitable non-irritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active ingredient(s).

Formulations of the pharmaceutical compositions which are suitable for vaginal administration also include pessaries, tampons, creams, gels, pastes, foams or spray formulations containing such carriers as are known in the art to be appropriate.

Topical administration may involve the use of transdermal administration such as transdermal patches or iontophoresis devices. Formulation of drugs is discussed in, for example, Hoover, J. E. Remington's pharmaceutical sciences, Mack Publishing Co., Easton, Pa., 1975; and Liberman, H. A.; Lachman, L., Eds. Pharmaceutical dosage forms, Marcel Decker, New York, N.Y., 1980, which are incorporated herein by reference in their entirety.

In other embodiments, the pharmaceutical composition having the presently disclosed compound(s), the salt thereof, the solvate thereof, the tautomer thereof, the stereoisomer thereof, prodrug thereof, or the mixture thereof has different release rates categorized as immediate release and controlled- or sustained-release.

As used herein, immediate release refers to the release of an active ingredient substantially immediately upon administration. In another embodiment, immediate release occurs when there is dissolution of an active ingredient within 1-20 minutes after administration. Dissolution can be of all or less than all (e.g. about 70%, about 75%, about 80%, about 85%, about 90%, about 91%, about 92%, about 93%, about 94%, about 95%, about 96%, about 97%, about 98%, about 99%, about 99.5%, 99.9%, or 99.99%) of the active ingredient. In another embodiment, immediate release results in complete or less than complete dissolution within about 1 hour following administration. Dissolution can be in a subject's stomach and/or intestine. In one embodiment, immediate release results in dissolution of an active ingredient within 1-20 minutes after entering the stomach. For example, dissolution of 100% of an active ingredient can occur in the prescribed time. In another embodiment, immediate release results in complete or less than complete dissolution within about 1 hour following rectal administration. In some embodiments, immediate release is through inhalation, such that dissolution occurs in a subject's lungs.

Controlled-release, or sustained-release, refers to a release of an active ingredient from a composition or dosage form in which the active ingredient is released over an extended period of time. In one embodiment, controlled-release results in dissolution of an active ingredient within 20-180 minutes after entering the stomach. In another embodiment, controlled-release occurs when there is dissolution of an active ingredient within 20-180 minutes after being swallowed. In another embodiment, controlled-release occurs when there is dissolution of an active ingredient within 20-180 minutes after entering the intestine. In another embodiment, controlled-release results in substantially complete dissolution after at least 1 hour following administration. In another embodiment, controlled-release results in substantially complete dissolution after at least 1 hour following oral administration. In another embodiment, controlled-release results in substantially complete dissolution after at least 1 hour following rectal administration. In one embodiment, the pharmaceutical composition described herein is not a controlled-release composition.

According to another aspect, the present disclosure relates to a method for treating a proliferative disorder. The method involves administering a therapeutically effective amount of one or more compounds of Formula (I) per se, or the pharmaceutical composition described above to a subject in need of therapy.

In one or more embodiments, the proliferative disorder is cancer. Types of cancers that may be treated with the compounds of the present disclosure include, but are not limited to, cancers of the stomach, breast, colon, brain, bladder, lung, cervix, ovary, rectum, pancreas, skin, prostate gland, spleen, liver, kidney, head, neck, testicle, bone, bone marrow, thyroid gland, and central nervous system. In some embodiments, the compounds of this disclosure can be used for the treatment of any cancer type that fails to undergo apoptosis in a subject. This includes, but is not limited to: solid tumors, including but not limited to carcinomas; sarcomas including Kaposi's sarcoma and osteosarcoma; erythroblastoma; glioblastoma; meningioma; astrocytoma; melanoma; and myoblastoma.

Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, hepatocellular carcinoma, gall bladder carcinoma, bronchial carcinoma, small cell lung carcinoma, non-small cell lung carcinoma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma. In preferred embodiments, the cancer that may be treated with the compounds of Formula (I) is lung cancer, breast cancer, and/or colon/colorectal cancer.

As used herein, the terms "treat", "treatment", and "treating" in the context of the administration of a therapy to a subject in need thereof refer to the reduction or inhibition of the progression and/or duration of a disease (e.g. cancer), the reduction or amelioration of the severity of the disease, and/or the amelioration of one or more symptoms thereof resulting from the administration of one or more therapies. "Treating" or "treatment" of the disease includes preventing the disease from occurring in a subject that may be predisposed to the disease but does not yet experience or exhibit symptoms of the disease (prophylactic treatment), inhibiting the disease (slowing or arresting its development), ameliorating the disease, providing relief from the symptoms or side-effects of the disease (including palliative treatment), and relieving the disease (causing regression of the disease). With regard to the disease, these terms simply mean that one or more of the symptoms of the disease will be reduced. Such terms may refer to one, two, three, or more results following the administration of one, two, three, or more therapies: (1) a stabilization, reduction (e.g. by more than 10%, 20%, 30%, 40%, 50%, preferably by more than 60% of the population of cancer cells and/or tumor size before administration), or elimination of the cancer cells, (2) inhibiting cancerous cell division and/or cancerous cell proliferation, (3) relieving to some extent (or, preferably, eliminating) one or more symptoms associated with a pathology related to or caused in part by unregulated or aberrant cellular division, (4) an increase in disease-free, relapse-free, progression-free, and/or overall survival, duration, or rate, (5) a decrease in hospitalization rate, (6) a decrease in hospitalization length, (7) eradication, removal, or control of primary, regional and/or metastatic cancer, (8) a stabilization or reduction (e.g. by at least 10%, 20%, 30%, 40%, 50%, 60%, 70%, preferably at least 80% relative to the initial growth rate) in the growth of a tumor or neoplasm, (9) an impairment in the formation of a tumor, (10) a reduction in mortality, (11) an increase in the response rate, the durability of response, or number of patients who respond or are in remission, (12) the size of the tumor is maintained and does not increase or increases by less than 10%, preferably less than 5%, preferably less than 4%, preferably less than 2%, (13) a decrease in the need for surgery (e.g. colectomy, mastectomy), and (14) preventing or reducing (e.g. by more than 10%, more than 30%, preferably by more than 60% of the population of metastasized cancer cells before administration) the metastasis of cancer cells.

The term "subject" and "patient" are used interchangeably. As used herein, they refer to any subject for whom or which therapy, including with the compositions according to the present disclosure is desired. In most embodiments, the subject is a mammal, including but not limited to a human, a non-human primate such as a chimpanzee, a domestic livestock such as a cattle, a horse, a swine, a pet animal such as a dog, a cat, and a rabbit, and a laboratory subject such as a rodent, e.g. a rat, a mouse, and a guinea pig. In preferred embodiments, the subject is a human.

As used herein, a subject in need of therapy includes a subject already with the disease, a subject which does not yet experience or exhibit symptoms of the disease, and a subject predisposed to the disease. In preferred embodiments, the subject is a person who is predisposed to cancer, e.g. a person with a family history of cancer. People who (i) smoke or regularly breathe in second-hand smoke, (ii) exposed to carcinogens such as asbestos, radioactive substances (e.g., uranium, radon), and/or (iii) inhaled chemicals or minerals (e.g., arsenic, beryllium, cadmium, silica, vinyl chloride, nickel compounds, chromium compounds, coal products, mustard gas, and chloromethyl ethers) are at a higher risk of contracting lung cancer. People who have been diagnosed with Human papillomavirus (HPV) are at a higher risk of contracting cervical cancer. A person with (i) chronic infection with the hepatitis B virus (HBV) or hepatitis C virus (HCV), (ii) cirrhosis of the liver, (iii) nonalcoholic fatty liver disease, and/or (iv) exposure to aflatoxins is at a higher risk of contracting liver cancer.

In one or more embodiments, the subject refers to a cancer patient who is currently undergoing, or has completed one or more chemotherapy regimens. In some embodiments, the subject has been previously administered/treated with, or is being currently administered/treated with, a thymidylate synthase inhibitor (e.g., capecitabine, fluorouracil (5-FU)), a thymidine phosphorylase (TPase) inhibitor (e.g., tipiracil, trifluridine), a topoisomerase I inhibitor (e.g., irinotecan), a topoisomerase II inhibitor (e.g., doxorubicin), a DNA synthesis inhibitor (e.g., oxaliplatin), a DNA crosslinking agent (e.g., cisplatin), and/or a targeted therapy (e.g., cetuximab, bevacizumab, panitumumab, zivaflibercept, ramucirumab). In preferred embodiments, the subject has been previously administered/treated with, or is being currently administered/treated with, a DNA crosslinking agent (e.g., cisplatin) and developed drug resistance via mechanisms related to decreased intracellular uptake, increased reflux, increased inactivation by sulfhydryl molecules such as glutathione, increased excision of the adducts from DNA by repair pathways, increased lesion bypass, and/or altered expression of regulatory proteins involved in signal transduction pathways that control the apoptotic processes.

In another embodiment, the subject refers to a cancer patient who has been previously administered and/or treated with a platinum-based chemotherapy drug such as Carboplatin, Oxaliplatin, Nedaplatin, Phenanthriplatin, Picoplatin, Satraplatin, Lipoplatin, and cisplatin, and developed resistance to the drug. In some embodiments, the subject refers to a cancer patient who has been previously treated and/or administered with cisplatin and develops cisplatin resistance due to reduced intracellular drug accumulation, overexpression of HER-2/neu and the PI3-K/Akt pathway, increase in DNA damage repair, dysfunction of tumor-suppressor p53, loss of pAMT function, and/or overexpression of antiapoptotic bcl-2. In at least one embodiment, the subject has lung, cervical, and/or cervical cancer and is currently undergoing, or has completed a cisplatin-based chemotherapy regimen.

The terms "administer", "administering", "administration", and the like, as used herein, refer to the methods that may be used to enable delivery of the active ingredient and/or the composition to the desired site of biological action. Routes or modes of administration are as set forth herein. These methods include, but are not limited to, oral routes, intraduodenal routes, parenteral injection (including intravenous, subcutaneous, intraperitoneal, intramuscular, intravascular, or infusion), topical and rectal administration. Those of ordinary skill in the art are familiar with administration techniques that can be employed with the complexes and methods described herein. In a preferred embodiment, the active ingredient and/or the pharmaceutical composition described herein are administered orally.

The dosage amount and treatment duration are dependent on factors, such as bioavailability of a drug, administration mode, toxicity of a drug, gender, age, lifestyle, body weight, the use of other drugs and dietary supplements, the disease stage, tolerance and resistance of the body to the administered drug, etc., and then determined and adjusted accordingly. The terms "effective amount", "therapeutically effective amount", or "pharmaceutically effective amount" refer to that amount of the active ingredient being administered which will relieve to some extent one or more of the symptoms of the disease being treated. The result can be a reduction and/or alleviation of the signs, symptoms, or causes of a disease, or any other desired alteration of a biological system. An appropriate "effective amount" may differ from one individual to another. An appropriate "effective amount" in any individual case may be determined using techniques, such as a dose escalation study. Typically, an effective amount of the compound disclosed herein is in a range of 0.01-100 mg/kg, preferably 0.05-90 mg/kg, preferably 0.1-80 mg/kg, preferably 0.5-70 mg/kg, preferably 1-60 mg/kg, preferably 2-50 mg/kg, preferably 3-40 mg/kg, preferably 4-30 mg/kg, preferably 5-20 mg/kg, preferably 6-10 mg/kg, preferably 7-8 mg/kg is administered per body weight of the subject. However, in certain embodiments, the effective amount of the compound is less than 0.01 mg/kg or greater than 100 mg/kg.

In treating certain cancers, the best approach is often a combination of surgery, radiotherapy, and/or chemotherapy. Therefore, in at least one embodiment, the pharmaceutical composition is employed in conjunction with radiotherapy. In another embodiment, the pharmaceutical composition is employed with surgery. The radiotherapy and/or surgery may be performed before or after the pharmaceutical composition is administered.

In some embodiments, the compound of the present disclosure is co-administered with radiation therapy or a second therapeutic agent with cytostatic or antineoplastic activity. Suitable cytostatic chemotherapy compounds include, but are not limited to (i) antimetabolites; (ii) DNA-fragmenting agents, (iii) DNA-crosslinking agents, (iv) intercalating agents (v) protein synthesis inhibitors, (vi) topoisomerase I poisons, such as camptothecin ortopotecan; (vii) topoisomerase II poisons, (viii) microtubule-directed agents, (ix) kinase inhibitors (x) miscellaneous investigational agents (xi) hormones, (xii) hormone antagonists, and (xii) targeted therapies. It is contemplated that compounds of the disclosure may be useful in combination with any known agents falling into the above 13 classes as well as any future agents that are currently in development. In particular, it is contemplated that compounds of the disclosure may be useful in combination with current Standards of Care as well as any that evolve over the foreseeable future. Specific dosages and dosing regimens would be based on physicians' evolving knowledge and the general skill in the art.

Examples of second therapeutic agents include, but are not limited to, a mitotic inhibitor; an alkylating agent; an antimetabolite; a cell cycle inhibitor; an enzyme; a topoisomerase inhibitor; a biological response modifier; an anti-hormone; a tubulin inhibitor; a tyrosine-kinase inhibitor; an antiangiogenic agent such as MMP-2, MMP-9 and COX-2 inhibitor; an anti-androgen; a platinum coordination complex (oxaliplatin, carboplatin, cisplatin); a substituted urea such as hydroxyurea; a methylhydrazine derivative; an adrenocortical suppressant, e.g., mitotane, aminoglutethimide; a hormone and/or hormone antagonist such as the adrenocorticosteriods (e.g., prednisone), progestins (e.g., hydroxyprogesterone caproate), an estrogen (e.g., diethylstilbestrol); an antiestrogen such as tamoxifen; androgen, e.g., testosterone propionate; and an aromatase inhibitor, such as anastrozole, and AROMASIN (exemestane); a thymidylate synthase inhibitor; a thymidine phosphorylase (TPase) inhibitor; a DNA synthesis inhibitor; and/or a targeted therapy. Exemplary second therapeutic agents include, but are not limited to, tubulin binding agents including paclitaxel, epothilone, docetaxel, discodermolide, etoposide, vinblastine, vincristine, teniposide, vinorelbine, and vindesine; tyrosine-kinase inhibitors including imatinib, nilotinib, dasatinib, bosutinib, ponatinib, and bafetinib; alkylating antineoplastic agents including busulfan, carmustine, chlorambucil, cyclophosphamide, cyclophosphamide, dacarbazine, ifosfamide, lomustine, mechlorethamine, melphalan, mercaptopurine, procarbazine; antimetabolites including cladribine, cytarabine, fludarabine, gemcitabine, pentostatin, 5-fluorouracil, clofarabine, capecitabine, methotrexate, thioguanine; cytotoxic antibiotics including daunorubicin, doxorubicin, idarubicin, mitomycin, actinomycin, epirubicin; topoisomerase inhibitors including irinotecan, mitoxantrone, topotecan; thymidine phosphorylase (TPase) inhibitors such as tipiracil and trifluridine; DNA synthesis inhibitors such as oxaliplatin; targeted therapies such as cetuximab, bevacizumab, panitumumab, zivaflibercept, ramucirumab; and mixtures thereof.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intratumoral routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Any other administration route combination is also contemplated herein according to the administration routes available for each of the therapeutic agents. Combination therapy also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

A treatment method may comprise administering a pharmaceutical composition containing the compound of the current disclosure in any of its embodiments as a single dose or multiple individual divided doses. In some embodiments, the composition is administered at various dosages (e.g. a first dose with an effective amount of 50 mg/kg and a second dose with an effective amount of 10 mg/kg). In some embodiments, the interval of time between the administration of the composition and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months, 5 months, 6 months, 7 months, 8 months, 9 months, 10 months, 11 months, 12 months, 1 year, 2 years, or any period of time in between. Preferably, the composition is administered once daily for at least 2 days, at least 5 days, at least 6 days, or at least 7 days. In certain embodiments, the composition and one or more additional therapies are administered less than 1 day, less than 1 week, less than 2 weeks, less than 3 weeks, less than 4 weeks, less than 1 month, less than 2 months, less than 3 months, less than 6 months, less than 1 year, less than 2 years, or less than 5 years apart.

The methods for treating cancer and other proliferative disorders described herein inhibit, remove, eradicate, reduce, regress, diminish, arrest or stabilize a cancerous tumor, including at least one of the tumor growth, tumor cell viability, tumor cell division and proliferation, tumor metabolism, blood flow to the tumor and metastasis of the tumor. In some embodiments, the size of a tumor, whether by volume, weight or diameter, is reduced after the treatment by at least 5%, at least 10%, at least 15%, at least 20%, at least 25%, at least 30%, at least 40%, at least 50%, at least 60%, at least 70%, at least 75%, at least 80%, at least 85%, at least 90%, at least 95%, at least 99%, or 100%, relative to the tumor size before treatment. In other embodiments, the size of a tumor after treatment does not reduce but is maintained the same as the tumor size before treatment. Methods of assessing tumor size include, but are not limited to, CT scan, MRI, DCE-MRI, PET scan, and manual tumor measurement.

In most embodiments, the method further involves measuring a concentration of a biomarker and/or detecting a mutation in a biomarker before and/or after the pharmaceutical composition comprising the compound of the present disclosure is administered. As used herein, the term "biomarker" refers to a characteristic that is objectively measured and evaluated as an indicator of normal biological processes, pathogenic processes or pharmacological responses to a therapeutic intervention. Generic cancer biomarkers include circulating tumor DNA (ctDNA) and circulating tumor cells (CTC). Exemplary biomarkers for lung cancer include, without limitation, CYFRA 21-1 (cytokeratins), EPCAM (epithelial cell adhesion molecule), ProGRP (pro-gastrin-releasing peptide), and CEACAM (carcinoembryonic antigen). Exemplary biomarkers for cervical cancer include, without limitation HPV E6, HPV E7, Mini chromosome maintenance (MCM), Cell division cycle protein 6 (CDC6), p16$^{Ink4A}$, Squamous cell carcinoma antigen (SCC), and Ki-67. Exemplary biomarkers for liver cancer include, without limitation, alpha-fetoprotein (AFP), AFP-L3, des-γ-carboxyprothrombin (DCP), GPC3, GP73, cytokeratin 19 (CK 19), osteopontin, IL-6, midkine (MDK), and Annexin A2.

The mutation in the biomarker may be detected by procedures such as restriction fragment length polymorphism (RFLP), polymerase chain reaction (PCR) assay, multiplex ligation-dependent probe amplification (MLPA), denaturing gradient gel electrophoresis (DGGE), single-strand conformation polymorphism (SSCP), hetero-duplex analysis, protein truncation test (PTT), and oligonucleotide ligation assay (OLA). The procedures to detect the mutation are well-known to those of ordinary skill in the art.

The term "sample" used herein refers to any biological sample obtained from the subject in need of therapy including a single cell, multiple cells, fragments of cells, a tissue sample, and/or body fluid. Specifically, the biological sample may include red blood cells, white blood cells, platelets, hepatocytes, epithelial cells, endothelial cells, a skin biopsy, a mucosa biopsy, an aliquot of urine, saliva, whole blood, serum, plasma, lymph. In some embodiments, the biological sample is taken from a tumor.

The concentration level of the cancer biomarker in a sample may be measured by an assay, for example an immunoassay. Typical immunoassay methods include, without limitation, enzyme-linked immunosorbent assay (ELISA), enzyme-linked immunospot assay (ELISPOT), Western blotting, immunohistochemistry (IHC), immunocytochemistry, immunostaining, and multiple reaction monitoring (MRM) based mass spectrometric immunoassay. The protocol for measuring the concentration of the biomarker and/or detecting the mutation in the biomarker is known to those of ordinary skill, for example by performing the steps outlined in the commercially available assay kit sold by Sigma-Aldrich, Thermo Fisher Scientific, R & D Systems, ZeptoMetrix Inc., Cayman Inc., Abcam, Trevigen, Dojindo Molecular Technologies, Biovision, and Enzo Life Sciences.

In some embodiments, a concentration of the biomarker is measured before and after the administration. When the concentration of the biomarker is maintained, the method may further comprise increasing the effective amount of the compound of the present disclosure by at least 5%, at least 10%, or at least 30%, up to 50%, up to 60%, or up to 80% of an initial effective amount The subject may be administered with the increased dosage for a longer period (e.g. 1 week more, 2 weeks more, or 2 months more) than the duration prescribed with the initial effective amount.

In some embodiments, the mutation in the biomarker is detected before administering the composition to identify subjects predisposed to the disease. Alternatively, the biomarkers are measured/detected after each administration. For example, the measurement may be 1-5 minutes, 1-30 minutes, 30-60 minutes, 1-2 hours, 2-12 hours, 12-24 hours, 1-2 days, 1-15 weeks, 15-20 weeks, 20-30 weeks, 30-40 weeks, 40-50 weeks, 1 year, 2 years, or any period of time in between after the administration.

In some embodiments, the administration is stopped once the subject is treated.

The examples below are intended to further illustrate protocols for preparing, characterizing, and using the compounds of the present disclosure and are not intended to limit the scope of the claims.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

EXAMPLES

Discussion of Chemistry

Figure 3:
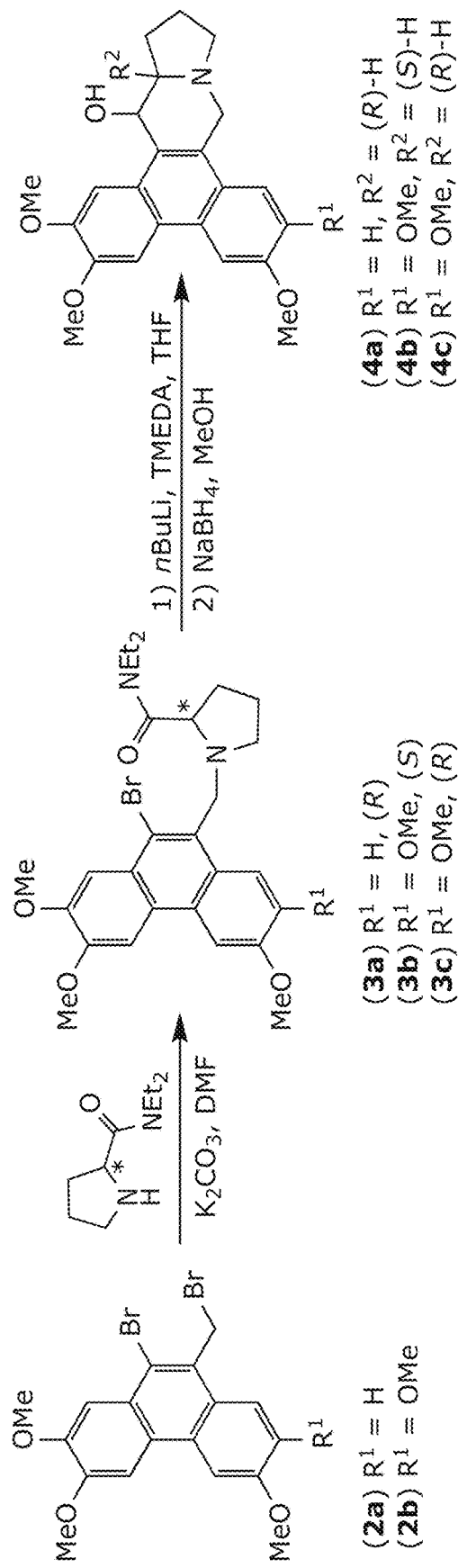
FIG. 3 shows the chemical synthesis of prodrugs 5a-c.
Figure 3:
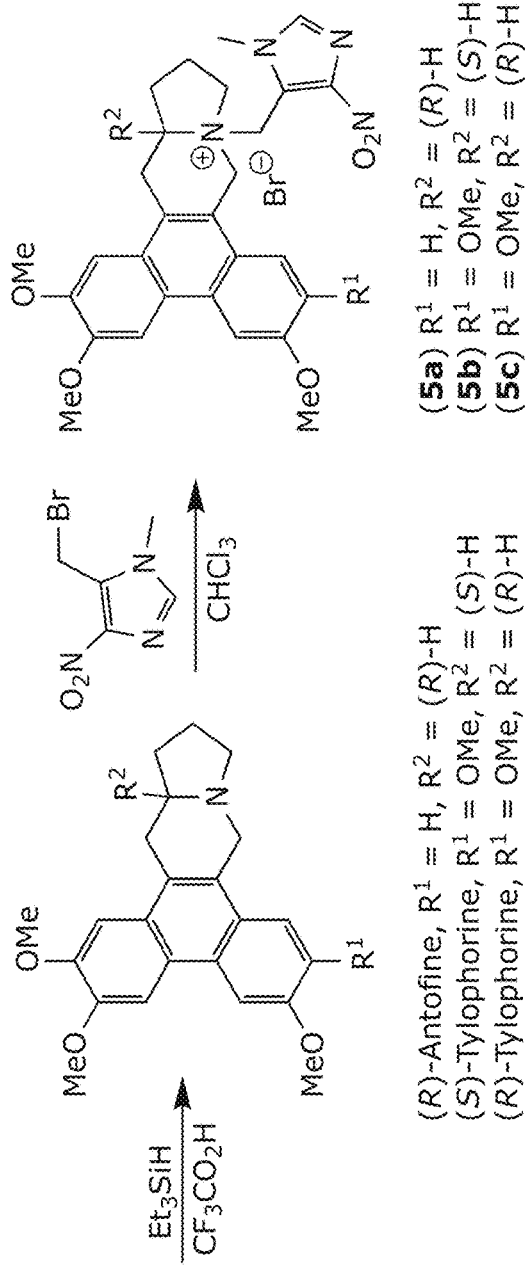

Both enantiomers of tylophorine and (R)-antofine were obtained as previously described with slight modification (FIG. 3). Briefly, dibromides 2 were alkylated by the corresponding N,N-diethylpyrrolidine-2-carboxamide. Amides 3 were then treated with nBuLi and TMEDA, followed by sodium borohydride, to yield alcohols 4, which were finally reduced using triethylsilane and trifluoroacetic acid to give the desired alkaloids. [Wang, Z., et. al., Eur. J. Org. Chem., 2010, 292-299, incorporated herein by reference in its entirety]. The target quaternary ammonium salts 5a-c were successfully synthesized by reacting appropriate precursor alkaloids with 5-(bromomethyl)-1-methyl-4-nitro-1H-imidazole. The prodrugs 5a-c obtained with reasonable yields (52-68%) after purification by silica gel.

Discussion of Physicochemical Properties

The physicochemical properties of the new compounds were evaluated (Table 1). The water solubility of the alkaloids was considerably increased, up to 80-fold, when they were transformed to their corresponding quaternary ammonium salts 5a-b. Consequently, these derivatives lost their BBB penetrability, as predicted by the BBB-Parallel Artificial Membrane Permeability Assay (BBB-PAMPA), whereas their parent alkaloids had free passage through the BBB. Additionally, the developed salts had significantly less affinity for plasma proteins than did their parent alkaloids.

TABLE 1

Physiochemical properties prodrugs 5a,b their parent alkaloids, and selected reference compounds.

| Compound | PBS (pH 7.4) Solubility μM Mean ± SE | LogD Mean ± SE | Permeability (Papp) Log [$10^{-6}$ cm/s] Mean ± SE | PPB (% of Bound Compound) Mean ± SE |
|---|---|---|---|---|
| 5a | 154 ± 0 | 0.69 ± 0.01 | <−7 | 87.0 ± 15 |
| 5b | 162 ± 3 | 0.38 ± 0.04 | <−7 | 58.9 ± 0.9 |
| (R)-Antofine | 27 ± 2 | 3.68 ± 0.03 | −5.6 ± 0.58 | 98.1 ± 0.15 |
| (S)-Tylophorine | 2 ± 0 | 3.14 ± 0.02 | −5.4 ± 0.17 | 93.9 ± 0.7 |
| Ondansetron (Reference) | 96 ± 3 | — | — | — |
| Mebendazole (Reference) | — | 3.26 ± 0.01 | — | — |
| Chlorpromazine (Reference) | — | — | −5.4 ± 0.13 | — |
| Clozapine (Reference) | — | — | −5.1 ± 0.12 | — |
| Ranitidine (Reference) | — | — | <−7 | — |
| Verapamil (Reference) | — | — | — | 89.4 ± 0.4 |

Figure 4A:
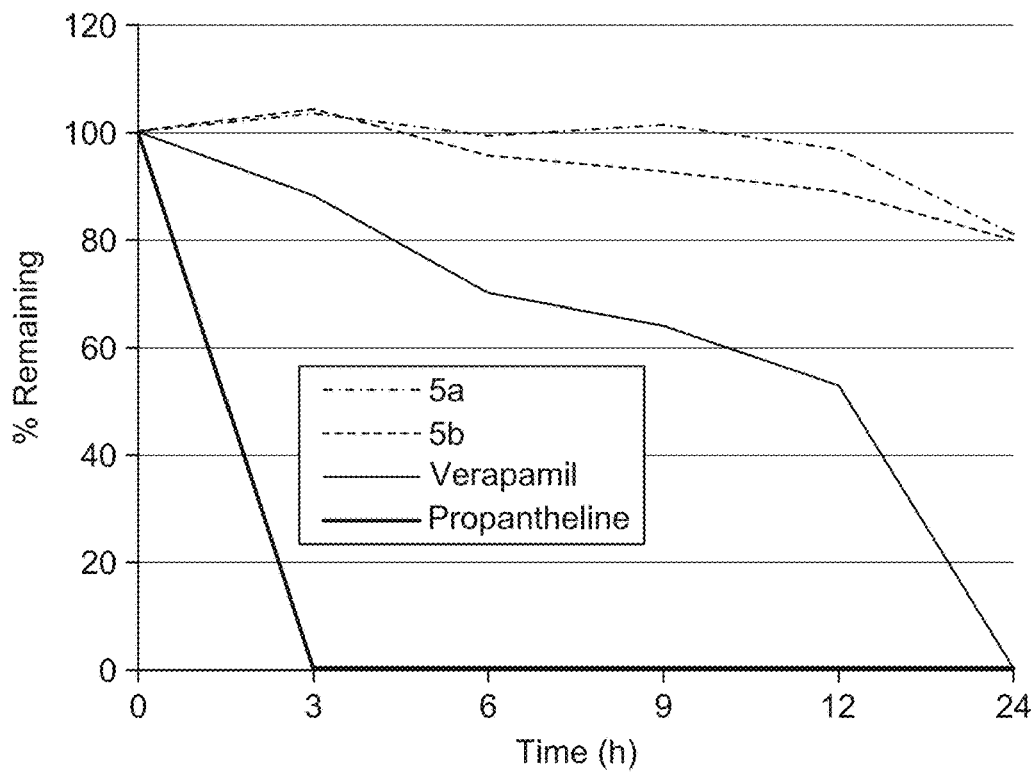
FIG. 4A shows the stability of prodrugs 5a,b in mouse plasma.
Figure 4B:
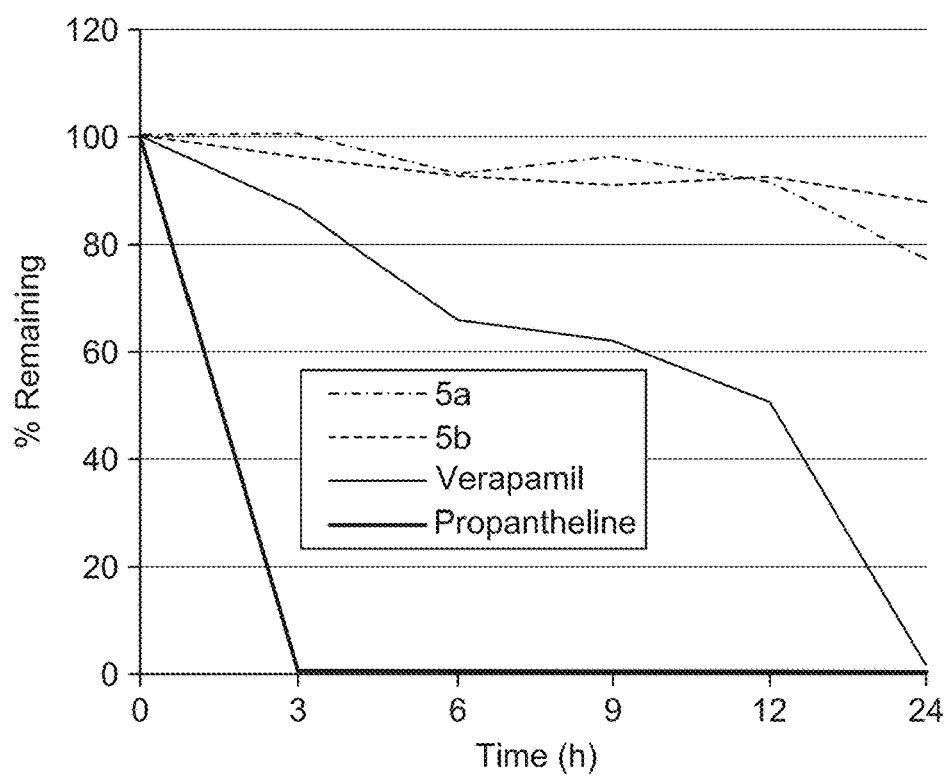
FIG. 4B shows the stability of prodrugs 5a,b in human plasma.

The chemical and metabolic stability of quaternary ammonium salts was also evaluated to ensure that the prodrugs would not be transformed into the parent alkaloids before arriving at their site of action, the hypoxic tumor. The developed prodrugs displayed high plasma stability when incubated with either mouse or human plasma (FIGS. 4-4B), attested by $t_{1/2}$ values ranging between 63 and 145 h, Table 2. Interestingly, after 24 h of incubation in either mouse or human plasma, no more than 1% of compounds 5a or 5b were transformed into their parent drugs.

TABLE 2

Mouse and human plasm stability for prodrugs 5a,b and selected reference compounds, $t_{1/2}$ half-life.

| Compound | $t_{1/2}$, h (Mouse Plasma) | $t_{1/2}$, h (Human Plasma) |
|---|---|---|
| 5a | 65.1 ± 0.7 | 144.7 ± 4.7 |
| 5b | 73.0 ± 1.7 | 63.3 ± 0.1 |
| Verapamil (Reference) | 13.0 ± 1.0 | 12.2 ± 0.4 |
| Propantheline (Reference) | <3 | <3 |

Figure 5:
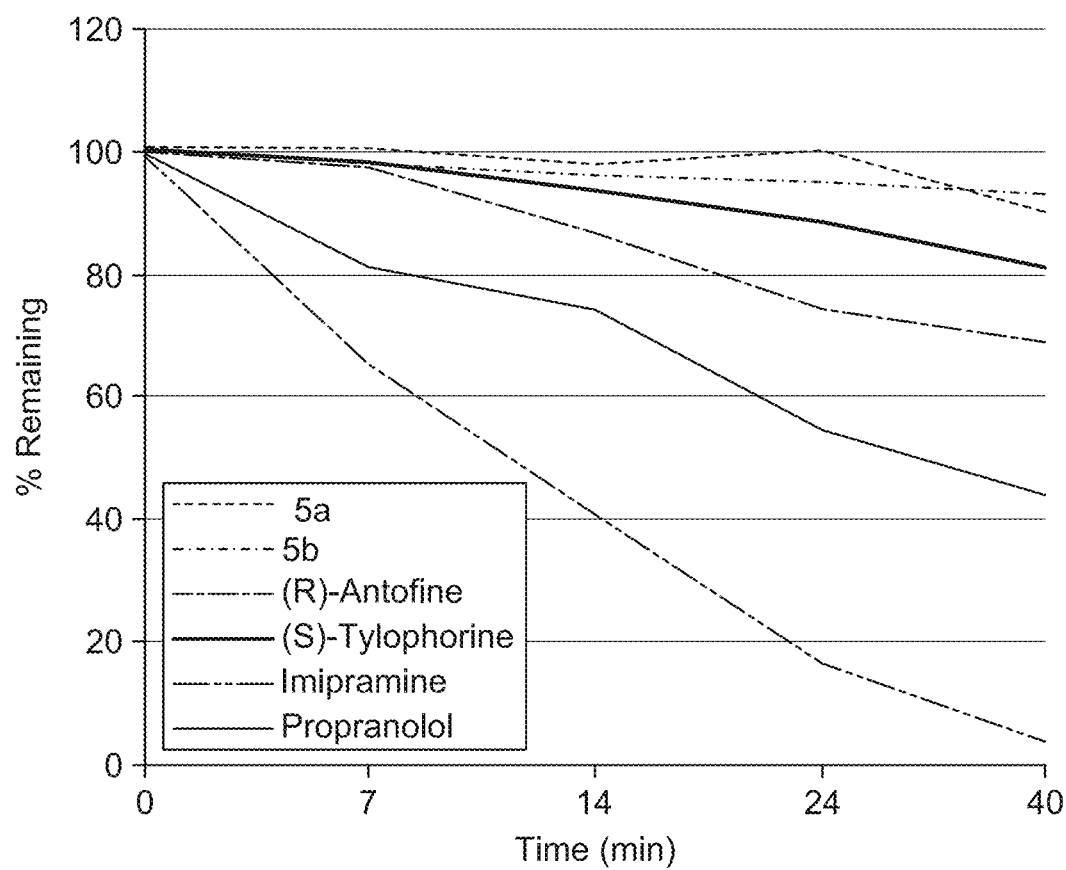
FIG. 5 shows the mouse hepatic microsomal stability for prodrugs 5a,b and their parent alkaloids.

Similarly, consistent with their reduced lipophilicity the developed quaternary ammonium salts showed significantly higher metabolic stability than was observed for their parent alkaloids following incubation with mouse liver microsomes (FIG. 5). The alkaloid half-lives were increased by three- to four-fold upon their transformation to the corresponding ammonium salts (Table 3). It is also noteworthy that less than 1% of compounds 5a or 5b was metabolized into the parent drug under these conditions.

TABLE 3

Mouse hepatic microsomal stability for prodrugs 5a,b, their parent alkaloids, and selected reference compounds. $K_{el}$: elimination rate constant, $t_{1/2}$: half-life.

| Compound | $K_{el}$, min$^{-1}$ | $t_{1/2}$, min |
| --- | --- | --- |
| 5a | 0.010 ± 0 | 286.9 ± 6.5 |
| 5b | 0.002 ± 0 | 404.0 ± 3.2 |
| (R)-Antofine | 0.002 ± 0 | 67.5 ± 2.1 |
| (S)-Tylophorine | 0.005 ± 0 | 127.5 ± 3.0 |
| Imipramine (Reference) | 0.083 ± 0 | 8.3 ± 0.4 |
| Propranolol (Reference) | 0.021 ± 0 | 33.5 ± 1.0 |

Discussion of Cytotoxic Activity

The cytotoxicity of the compounds 5a-c and their parent alkaloids was evaluated by the 3-[4,5-dimethylthiazole-2-yl]-2,5-diphenyltetrazolium bromide (MTT) assay against 5 cancerous and 2 non-cancerous cell lines (Table 4). All three quaternary ammonium salts 5a-c showed significantly decreased cytotoxicity (up to 1000-fold) against cancerous and noncancerous cell lines alike under normoxic conditions when compared with the parent drugs.

Figure 6A:
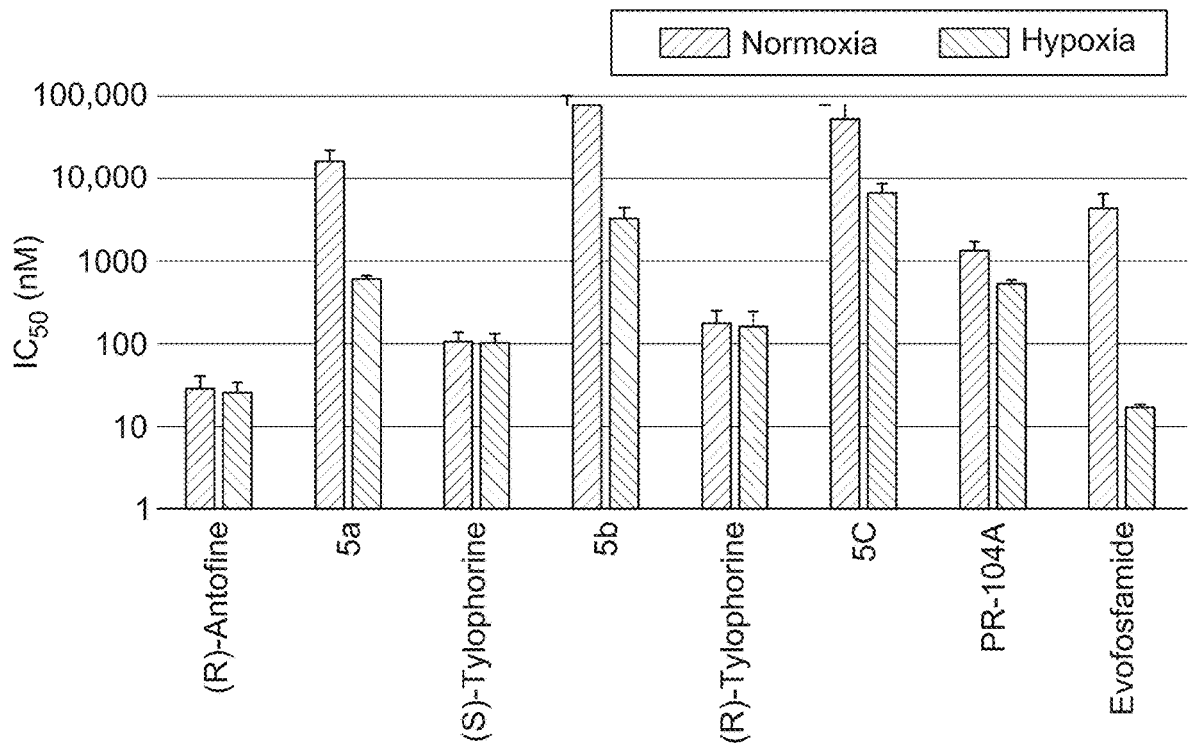
FIG. 6A-6B are plots of the cytotoxicity of compounds 5a-c and their parent alkaloids under normoxia and hypoxia against HCT116 (FIG. 6A) and H460 (FIG. 6B) (IC50, nM).
Figure 6B:
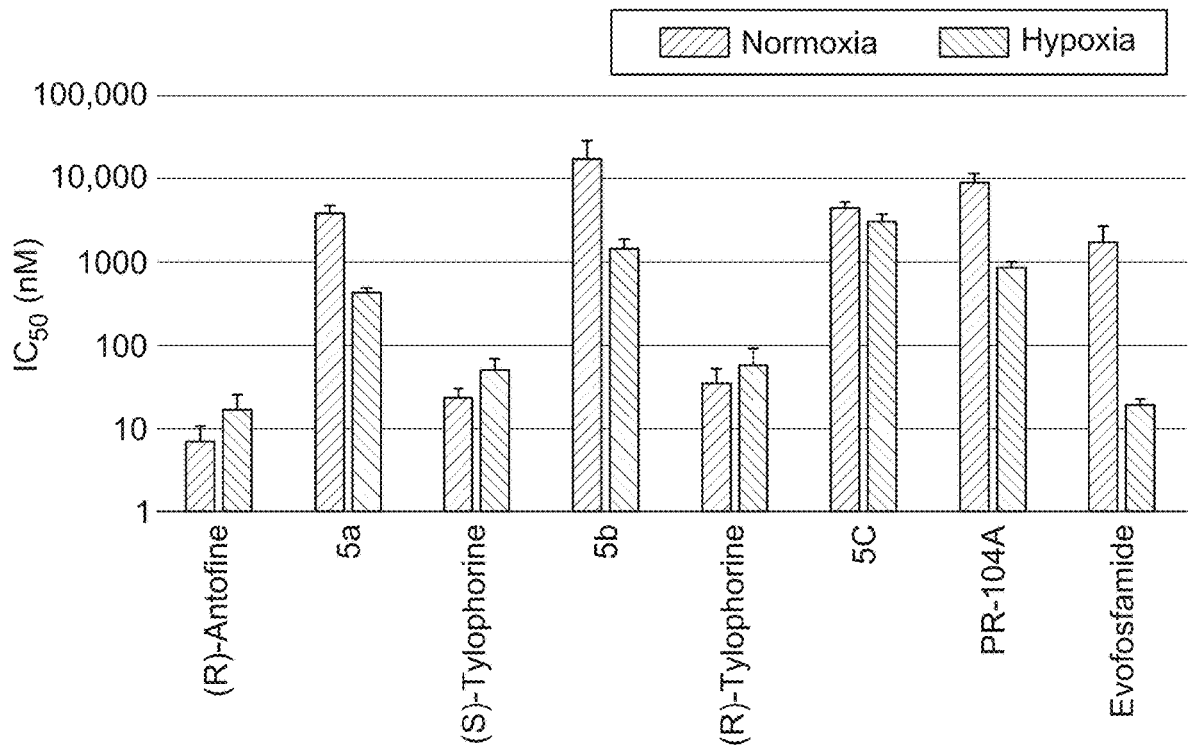

The ability of the designed prodrugs to liberate the active alkaloids in hypoxic tumors was evaluated by testing them under hypoxic conditions using an anaerobic chamber. The three prodrugs 5a-c and their parent alkaloids as well as the reference compounds PR-104A, the parent alcohol form of the phosphate pre-prodrug PR-104, and evofosfamide were tested using the HCT116 and H460 cell lines under both normoxic and hypoxic conditions (Table 5). The prodrugs were much less cytotoxic than the parent drugs, in agreement with the results using the other cell lines described above (see FIG. 6).

TABLE 4

Cytotoxicity of compounds 5a-c and their parent alkaloids under normoxia (nM, IC$_{50}$).

| Compound | HEK293 | CHO-K1 | MCF7 | HCT116 | RKO | SW480 | MRC5 |
| --- | --- | --- | --- | --- | --- | --- | --- |
| 5a | 5080 ± 519 | 1680 ± 542 | 1530 ± 144 | 1038 ± 21 | 2034 ± 267 | 1350 ± 0.126 | 327 ± 147 |
| 5b | 950 ± 174 | 3490 ± 843 | 1498 ± 128 | 3304 ± 1562 | 4056 ± 181 | 7245 ± 490 | 3313 ± 163 |
| 5c | — | — | 8050 ± 343 | 9019 ± 1128 | 8821 ± 3081 | 9862 ± 1693 | 3943 ± 127 |
| (R)-Antofine | 340 ± 43 | 33 ± 50 | 2 ± 0 | 2 ± 0 | 2 ± 0 | 9 ± 2 | 6 ± 2 |
| (S)-Tylophorine | 16 ± 26 | 35 ± 42 | 62 ± 13 | 85 ± 6 | 202 ± 3 | 69 ± 20 | 27 ± 2 |
| (R)-Tylophorine | — | — | 101 ± 88 | 440 ± 36 | 338 ± 61 | 1148 ± 244 | 95 ± 6 |

TABLE 5

Cytotoxicity of compounds 5a-c and their parent alkaloids under normoxia and hypoxia (IC50, nM).

| Cell Line Compound | HTC 116 | | | H460 | | |
| --- | --- | --- | --- | --- | --- | --- |
| | IC$_{50}$ (Normoxia) | DR | IC$_{50}$ (Hypoxia) | HCR | IC$_{50}$ (Normoxia) | DR | IC$_{50}$ (Hypoxia) | HCR |
| 5a | 16,471 ± 11,571 | 543 | 424.7 ± 51 | 8.8 | 15,847.0 ± 6,339 | 543 | 618.0 ± 44 | 26 |
| (R)-Antofine | 23.9 ± 7 | | 16.7 ± 9 | 0.4 | 29.2 ± 12 | | 25.4 ± 9 | 0.6 |
| 5b | 4,489.0 ± 698 | 689 | 1,463.3 ± 411 | 11.3 | 77,598.3 ± 22,402 | 719 | 3,220.0 ± 1,071 | 24 |
| (S)-Tylophorine | 35.1 ± 15 | | 50.1 ± 18 | 0.5 | 107.9 ± 28 | | 101.9 ± 32 | 1.1 |
| 5c | 9,055.0 ± 7,592 | 128 | 3,024.7 ± 656 | 1.5 | 51,024.7 ± 22,402 | 293 | 6,500.0 ± 1,812 | 7.8 |
| (R)-Tylophorine | 1,711.0 ± 965 | | 56.4 ± 35 | 0.6 | 174.9 ± 78 | | 160.9 ± 77 | 1.1 |
| PR-104A | 16,471.5 ± 11,571 | — | 860.7 ± 122 | 10.5 | 1,337 ± 386 | — | 533.0 ± 47 | 2.5 |
| Evofosfamide | 23.9 ± 7 | — | 20.1 ± 3 | 85 | 4,322.7 ± 1,931 | — | 17.2 ± 1 | 251 |

The extent to which a prodrug is deactivated relative to its parent drug under normoxic conditions is defined as the Deactivation Ratio (DR). The DR can be simply calculated as DR=IC50 (prodrug)/IC50 (parent drug). The developed prodrugs 5a-c displayed excellent DRs ranging between 128 and 719. When tested under hypoxic conditions, the parent antofine and tylophorine drugs showed similar cytotoxicities to those seen under normoxic conditions. By contrast, prodrugs 5a-c showed significantly higher cytotoxicity under hypoxia than under normoxia (Table 4).

The efficacy of prodrug activation under hypoxic conditions can be expressed by the Hypoxia Cytotoxicity Ratio (HCR), which can be calculated for a given prodrug as:

$$\text{HCR} = \text{normoxic IC}_{50} / \text{hypoxic IC}_{50} \quad (1)$$

Prodrugs 5a-c displayed interesting HCRs ranging between 1.5 and 26, thereby confirming the selectivity of these new derivatives for hypoxic tumors (Table 5).

Figure 7A:
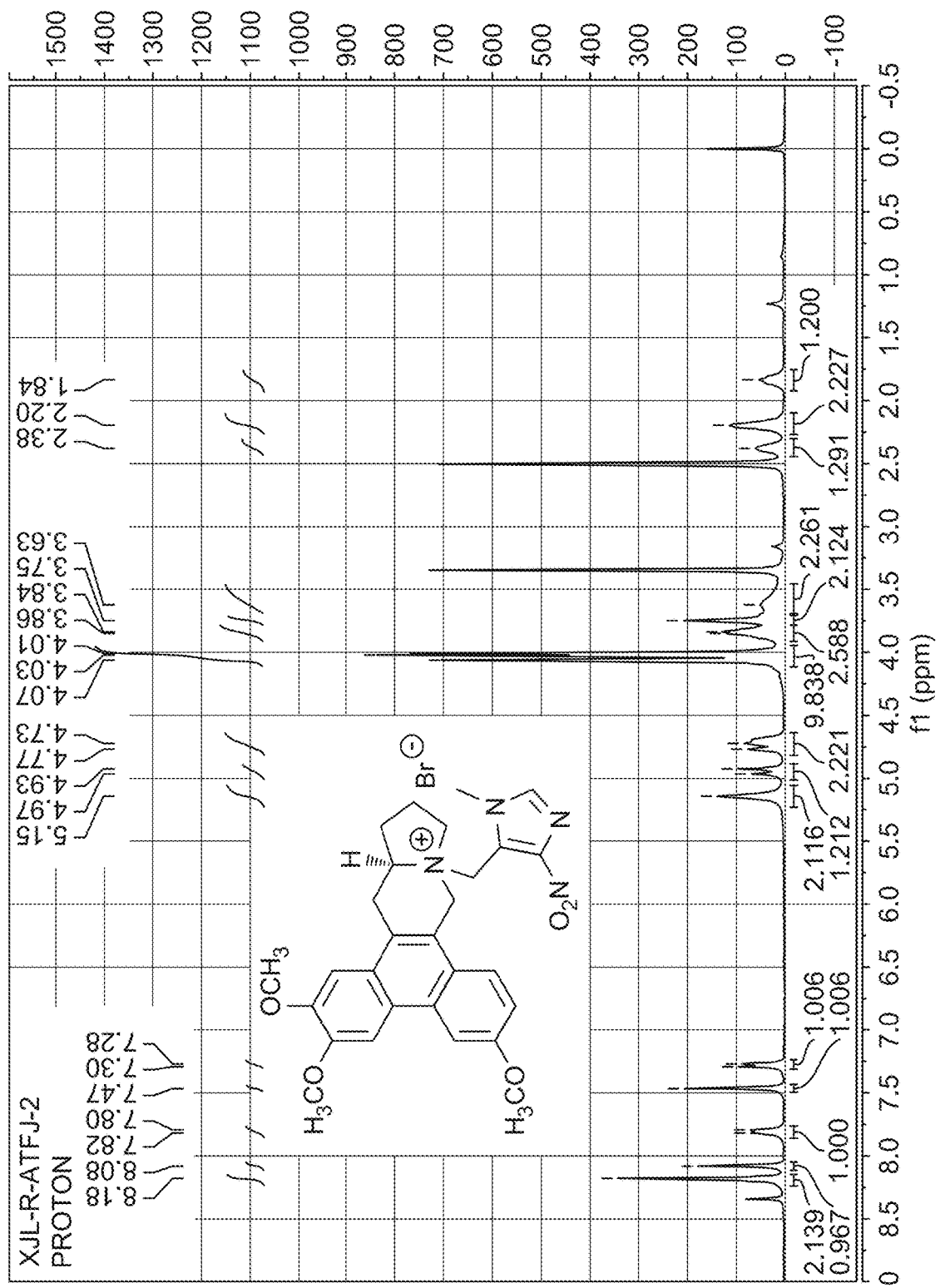
Figure 7B:
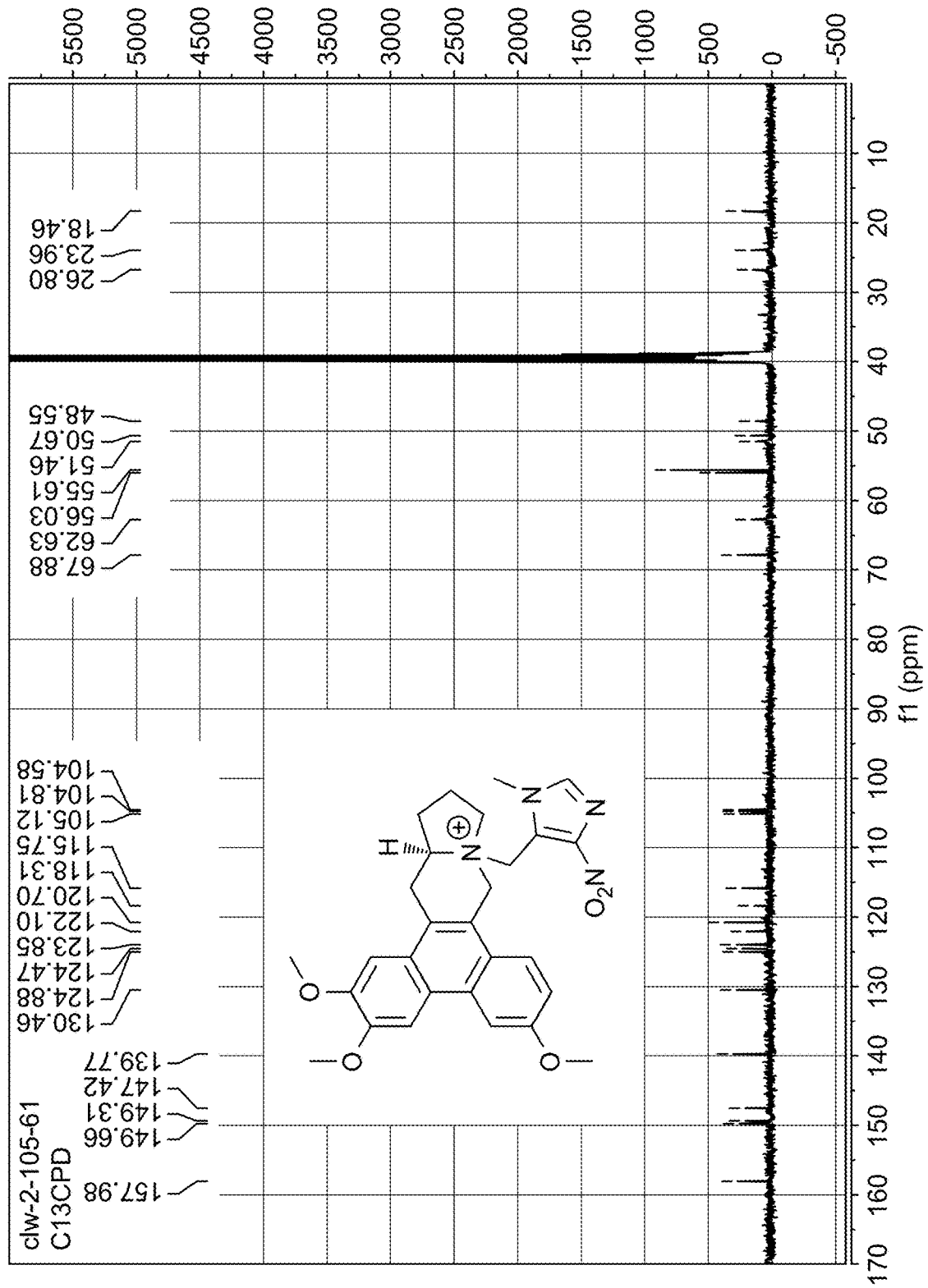
Figure 7C:
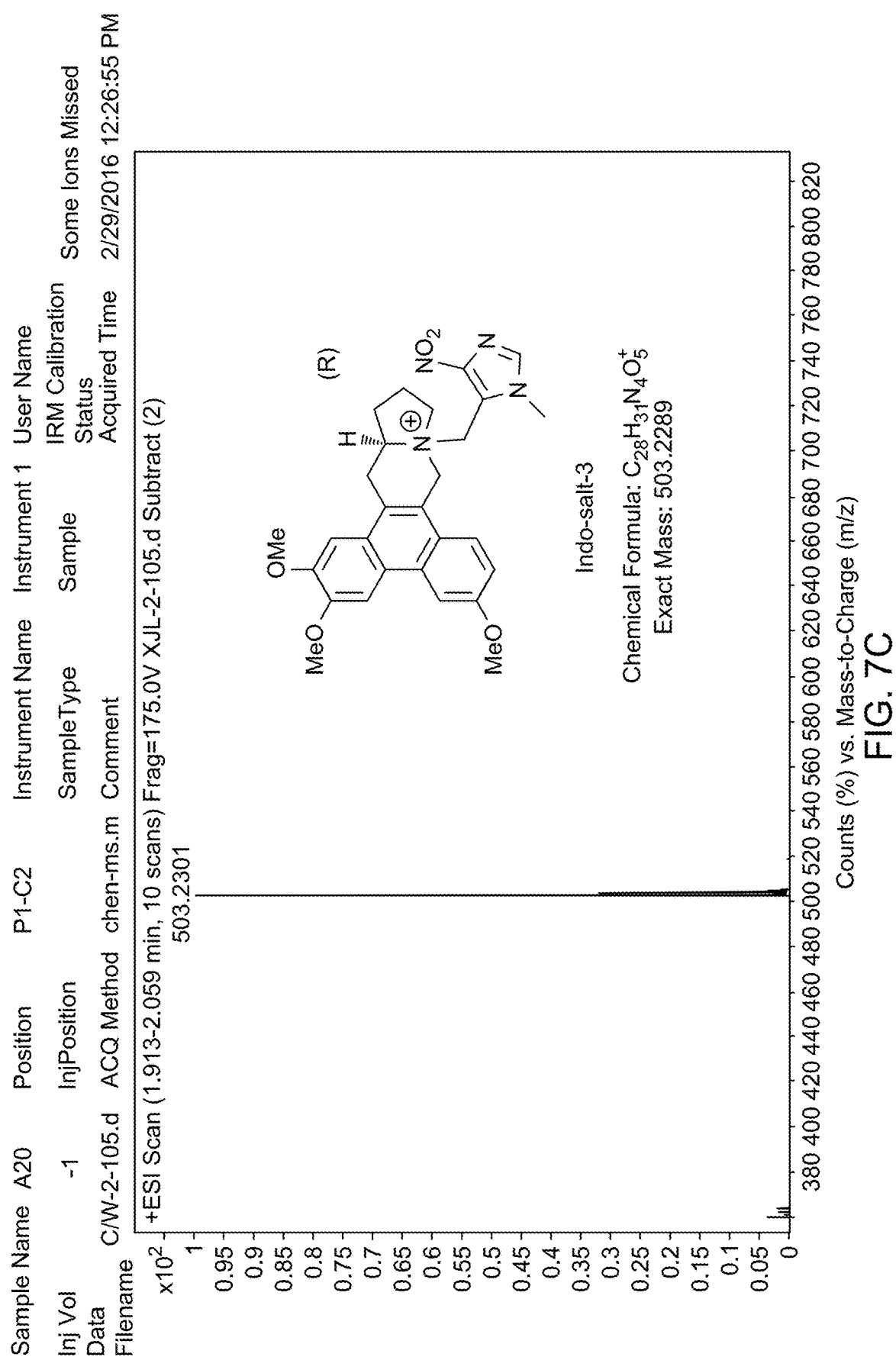

Synthetic Procedures (13aR)-2,3,6-trimethoxy-10-((1-methyl-4-nitro-1H-imidazol-5-yl)methyl)-10,11,12,13,13a, 14-hexahydro-9H-dibenzo[f,h]pyrrolo[1,2-b]isoquinolin-10-ium bromide (5a). To a solution of (R)-antofine (0.17 g, 0.48 mmol) in $CHCl_3$ (30 mL) was added 5-(bromomethyl)-1-methyl-4-nitro-1H-imidazole (0.16 g, 0.73 mmol), and the reaction mixture was heated at reflux for 20 h under an atmosphere of argon. After the mixture was evaporated under vacuum, the residue was purified by column chromatography on silica gel ($CH_2Cl_2$: $CH_3OH$=10:1) to give the quaternary ammonium salt as a yellow solid (yield 52%). Mp: 177-179° C.; purity: >99%; 1H-NMR (400 MHz, DMSO-d6) δ 8.24 (s, 2H), 8.14 (s, 1H), 7.87 (d, J=9.0 Hz, 1H), 7.53 (s, 1H), 7.33 (d, J=9.0 Hz, 1H), 5.21 (s, 2H), 5.01 (d, J=17.1 Hz, 1H), 4.87-4.70 (m, 2H), 4.12 (s, 3H), 4.08 (s, 3H), 4.06 (s, 3H), 3.90-3.45 (m, 7H), 2.50-2.37 (m, 1H), 2.32-2.20 (m, 2H), 1.98-1.80 (m, 1H). Spectrum presented in FIG. 7A. 13C-NMR (100 MHz, DMSO-d6) δ 158.0, 149.7, 149.3, 147.4, 139.8 (2C), 130.5, 124.9, 124.5, 123.9, 122.1, 120.7, 118.3, 115.8, 105.1, 104.8, 104.6, 67.9, 62.6, 56.0, 55.6, 51.5, 50.7, 33.3, 26.8, 24.0, 18.5. Spectrum presented in FIG. 7B. HRMS (ESI) calcd for $C_{29}H_{33}N_3O_5$ (M-Br)+503.2415, found 503.2301. Spectrum presented in FIG. 7C.

Figure 8A:
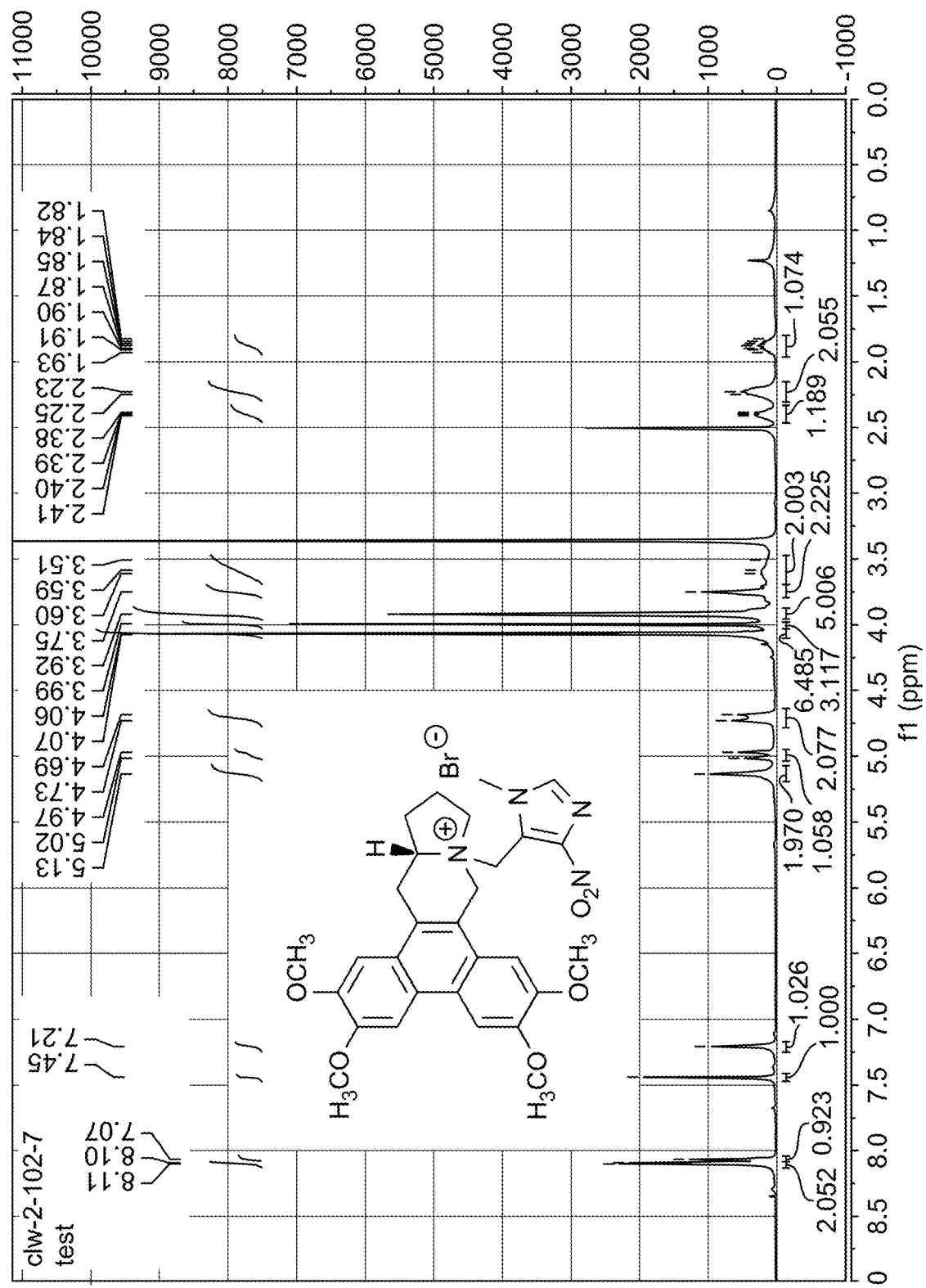
FIG. 8A shows the $^1$H-NMR spectrum of compound 5b.
Figure 8B:
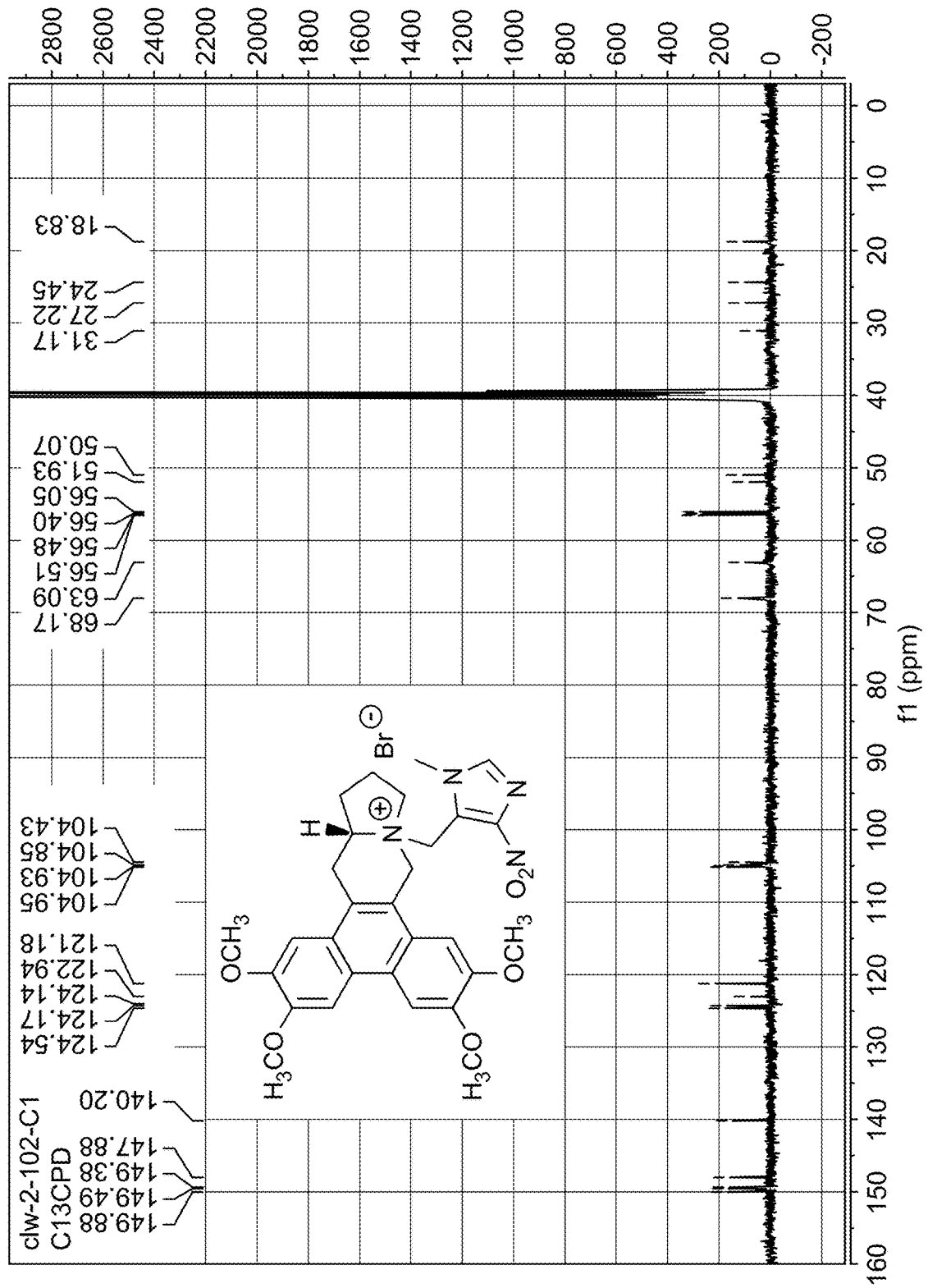
FIG. 8B shows the $^{13}$C-NMR spectrum of compound 5b.
Figure 8C:
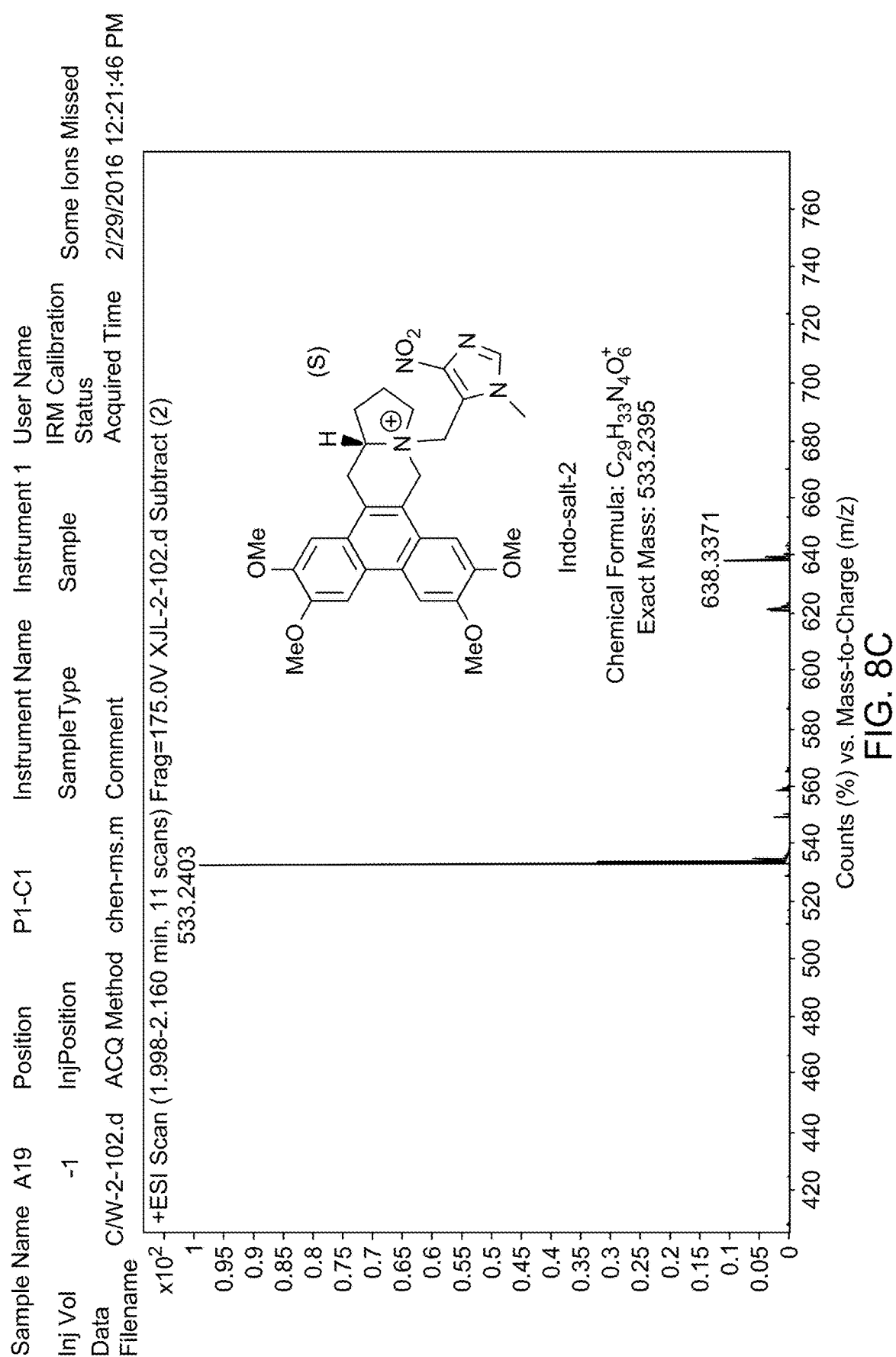
FIG. 8C shows the ESI mass spectrum of compound 5b.

(13aS)-2,3,6,7-tetramethoxy-10-((1-methyl-4-nitro-1H-imidazol-5-yl)methyl)-10,11,12,13,13a, 14-hexahydro-9H-dibenzo[f,h]pyrrolo[1,2-b]isoquinolin-10-ium bromide (5b). The synthetic procedure was similar to that of compound 5a. Compound 5b was obtained as yellow solid (0.17 g, 58%). Mp: 165-167° C.; purity: >99%; 1H-NMR (400 MHz, DMSO-d6) δ 8.11 (s, 1H), 8.10 (s, 1H), 8.07 (s, 1H), 7.45 (s, 1H), 7.21 (s, 1H), 5.13 (s, 2H), 4.99 (d, J=17.5 Hz, 1H), 4.76-4.66 (m, 2H), 4.07 (s, 3H), 4.06 (s, 3H), 3.99 (s, 3H), 3.96-3.85 (m, 5H), 3.81-3.69 (m, 2H), 3.69-3.49 (m, 2H), 2.46-2.15 (m, 3H), 1.94-1.80 (m, 1H). Spectrum presented in FIG. 8A. 13C-NMR (100 MHz, DMSO-d6) δ 149.9, 149.5, 149.4, 149.3, 147.9, 140.2, 124.5, 124.2, 124.1, 122.9, 121.2, 105.0, 104.93, 104.85, 104.4, 68.2, 63.1, 56.51, 56.48, 56.4, 56.1, 51.9, 51.0, 31.2, 27.2, 24.5, 18.8. Spectrum presented in FIG. 8B. HRMS (ESI) calcd for $C_{30}H_{35}N_3O_6$ (M-Br)+533.2520, found 533.2403. Spectrum presented in FIG. 8C.

Figure 9A:
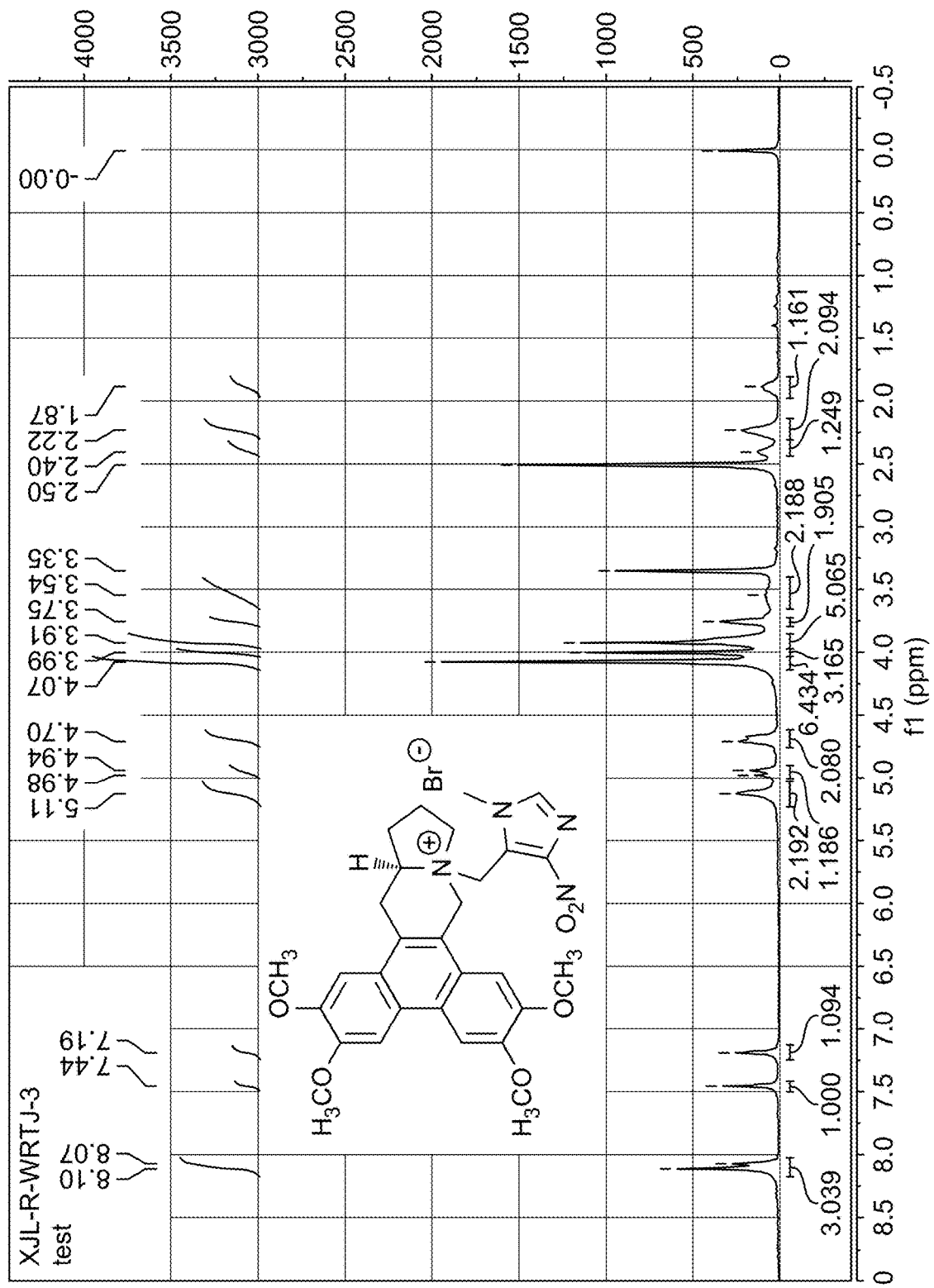
FIG. 9A shows the $^1$H-NMR spectrum of compound 5c.
Figure 9C:
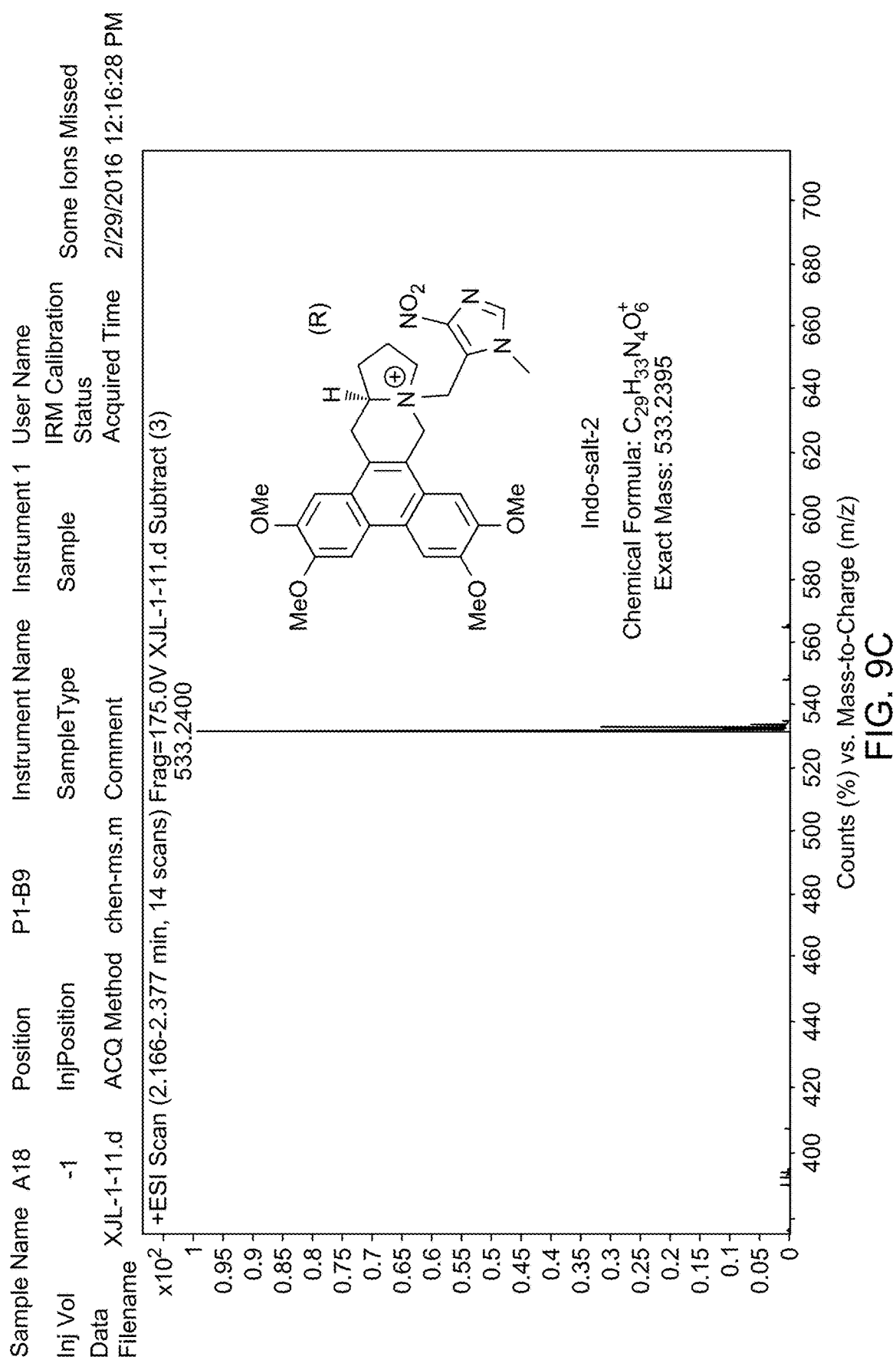
FIG. 9C shows the ESI mass spectrum of compound 5c.

(13aR)-2,3,6,7-tetramethoxy-10-((1-methyl-4-nitro-1H-imidazol-5-yl)methyl)-10,11,12,13,13a, 14-hexahydro-9H-dibenzo[f,h]pyrrolo[1,2-b]isoquinolin-10-ium bromide (5c). The synthetic procedure was similar to that of compound 5a. Compound 5c was obtained as yellow solid (yield 55%). Mp: 185-187° C.; purity: >99%; 1H-NMR (400 MHz, DMSO-d6) δ 8.11 (s, 1H), 8.10 (s, 1H), 8.08 (s, 1H), 7.45 (s, 1H), 7.20 (s, 1H), 5.13 (s, 2H), 4.98 (d, J=17.4 Hz, 1H), 4.80-4.62 (m, 2H), 4.07 (s, 6H), 4.00 (s, 3H), 3.96-3.84 (m, 5H), 3.82-3.68 (m, 2H), 3.67-3.42 (m, 2H), 2.46-2.14 (m, 3H), 1.94-1.81 (m, 1H). Spectrum presented in FIG. 9A. 13C-NMR (100 MHz, DMSO-d6) δ 149.9, 149.5, 149.4, 149.3, 147.9, 140.2, 124.5, 124.2, 124.1, 122.9, 121.2, 117.9, 104.92, 104.90, 104.8, 104.4, 68.2, 63.1, 56.50, 56.45, 56.4, 56.0, 51.8, 50.9, 49.1, 27.2, 24.4, 18.8. Spectrum presented in FIG. 9B. HRMS (ESI) calcd for $C_{30}H_{35}N_3O_6$ (M-Br)+533.2520, found 533.2400. Spectrum presented in FIG. 9C.

Characterization Techniques

Water solubility, log D, and PAMPA-BBB were evaluated using the protocols as described in Omran, et. al. [Omran, Z., et. al., Chem. Pharm. Bull., 2019, 67, 1208-1210, incorporated herein by reference in its entirety].

Mouse/Human Plasma Stability Test

Incubations were carried out in 6 aliquots of 70 µL each in duplicates. The test compounds (1 µM, final DMSO concentration 0.5%) were incubated at 37° C. with shaking at 100 rpm. Six time points over 24 h (0, 3, 6, 9, 12 and 24 h) have been analyzed. The reactions were stopped by adding 350 µL of acetonitrile with subsequent plasma proteins sedimentation by centrifuging at 5500 rpm for 5 min. Supernatants were analyzed by LC-MS using Shimadzu VP HPLC system including vacuum degasser, gradient pumps, reverse phase column, column oven and autosampler. The HPLC system was coupled with tandem mass spectrometer API 3000 (PE Sciex, Foster City, Calif., USA). Both the positive and negative ion modes of the TurbolonSpray ion source were used. The acquisition and analysis of the data were performed using Analyst 1.5.2 software (PE Sciex, API 3000 mass spectrometer, Foster City, Calif., USA). The percentage of the test compounds remaining after incubation in plasma and their half-lives (ty) were calculated.

Mouse Microsomal Liver Stability Assay

Mouse hepatic microsomes were isolated from pooled, perfused livers of Balb/c male mice according to the standard protocol as described in Hill, 2003 [Hill, J. R., Curr. Protoc. Pharmacol., 2003, 23, 7.8.1-7.8.11, incorporated herein by reference in its entirety]. The batch of microsomes was tested for quality control using imipramine and propranolol as reference compounds. Microsomal incubations were carried out in 96-well plates in 5 aliquots of 40 µL each. Liver microsomal incubation medium contained PBS (100 mM, pH 7.4), $MgCl_2$ (3.3 mM), NADPH (3 mM), glucose-6-phosphate (5.3 mM), glucose-6-phosphate dehydrogenase (0.67 units/mL) with 0.42 mg of liver microsomal protein per ml. Control incubations were performed by replacing the NADPH-cofactor system with PBS. The additional control incubations in PBS (with 3.3 mM $MgCl_2$) without added microsomes were carried out in this study. Test compound (2 µM, final solvent concentration 1.6%) was incubated with microsomes at 37° C., shaking at 100 rpm. The incubations were performed in duplicates. Five time points over 40 min had been analyzed. The reactions were stopped by adding 12 volumes of 90% acetonitrile-water to incubation aliquots, followed by protein sedimentation by centrifuging at 5500 rpm for 3 min. The supernatants were analyzed using LC-MS as mentioned above.

Cytotoxicity Assay

The eight cell lines HEK293 (Human embryonic kidney 293), CHO-Kt (Chinese hamster ovary K1), MCF-7 cells (Human breast adenocarcinoma), HCT116 (human colorectal carcinoma), RKO (Human rectal carcinoma), SW480 (human colorectal carcinoma), H460 (Human lung cancer), and MRCS (Normal human fetal lung fibroblast), were obtained from the ATCC. The cell lines were routinely grown in alpha minimum essential medium (α-MEM) containing 5% fetal calf serum (FCS). The appropriate number of cells (HCT116=400 cells/well, H460 cells=600 cells/well) were seeded into 96-well plates under normoxic or hypoxic conditions. Cells were plated in 100 µL α-MEM containing 10% FCS, 10 mM D-Glucose and 0.2 mM 20-deoxycytidine. After incubation for 2 h, the compounds were added at the appropriate concentration and incubated for further 4 h. The cells were then washed three times with drug-free α-MEM (containing 5% FCS and pen/strep). The plates were then incubated for 5 days under normoxic conditions. The cells were stained with sulphorhodamine B to measure total cells as per the standard procedure described in Skehan, et. al. [Skehan, P., et. al., J. Natl. Cancer Inst., 1990, 82, 1107-1112, incorporated herein by reference in its entirety]. The $IC_{50}$ was determined by interpolation as the compound concentration reducing staining to 50% of controls on the same plate as per the standard procedure described in Guise, et. al. [Guise, C. P., et. al., Biochem. Pharmacol., 2007, 74, 810-820, incorporated herein by reference in its entirety].

The invention claimed is:
1. A compound having a structure of Formula (I):

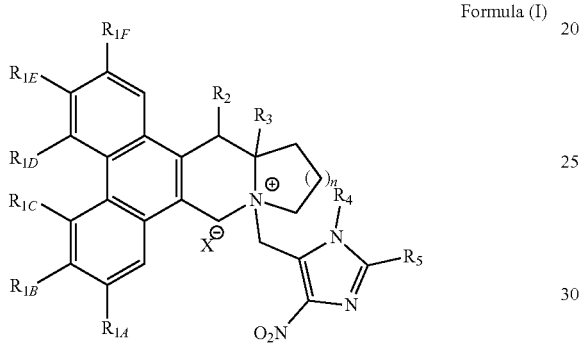

Formula (I)

or a pharmaceutically acceptable salt or stereoisomer thereof,
wherein:
$R_{1A}$ is H, OH, or $OC_1$-$C_8$ alkyl, wherein the $OC_1$-$C_8$ alkyl is optionally substituted with one or more substituents independently selected from the group consisting of halo, CN, $NO_2$, C(O)alkyl, C(O)$NH_2$, C(O)NH(alkyl), C(O)NH(aralkyl), C(O)NH(aryl), C(O)N(alkyl)$_2$, C(O)N(aralkyl)$_2$, C(O)N(aryl)$_2$, C(O)OH, C(O)O(alkyl), $NH_2$, NH(alkyl), NH(aralkyl), NHC(NH)$NH_2$, NHC(O)alkyl, NHC(O)aralkyl, NHC(O)aryl, NH(aryl), N(alkyl)$_2$, N(aralkyl)$_2$, N(aryl)$_2$, OH, O(alkyl), OC(O)alkyl, O(aryl), =O, SH, S(alkyl), S(aralkyl), S(aryl), S(O)alkyl, S(O)aralkyl, S(O)aryl, S(O)$_2$alkyl, S(O)$_2$aralkyl, S(O)$_2$$NH_2$, S(O)$_2$NH(alkyl), S(O)$_2$N(alkyl)$_2$, S(O)$_2$aryl, heterocyclyl, and aryl;

$R_{1B}$ is H, OH, or $OC_1$-$C_8$ alkyl, wherein the $OC_1$-$C_8$ alkyl is optionally substituted with one or more substituents independently selected from the group consisting of halo, CN, $NO_2$, C(O)alkyl, C(O)$NH_2$, C(O)NH(alkyl), C(O)NH(aralkyl), C(O)NH(aryl), C(O)N(alkyl)$_2$, C(O)N(aralkyl)$_2$, C(O)N(aryl)$_2$, C(O)OH, C(O)O(alkyl), $NH_2$, NH(alkyl), NH(aralkyl), NHC(NH)$NH_2$, NHC(O)alkyl, NHC(O)aralkyl, NHC(O)aryl, NH(aryl), N(alkyl)$_2$, N(aralkyl)$_2$, N(aryl)$_2$, OH, O(alkyl), OC(O)alkyl, O(aryl), =O, SH, S(alkyl), S(aralkyl), S(aryl), S(O)alkyl, S(O)aralkyl, S(O)aryl, S(O)$_2$alkyl, S(O)$_2$aralkyl, S(O)$_2$$NH_2$, S(O)$_2$NH(alkyl), S(O)$_2$N(alkyl)$_2$, S(O)$_2$aryl, heterocyclyl, and aryl;

$R_{1C}$ is H, OH, or $OC_1$-$C_8$ alkyl, wherein the $OC_1$-$C_8$ alkyl is optionally substituted with one or more substituents independently selected from the group consisting of halo, CN, $NO_2$, C(O)alkyl, C(O)$NH_2$, C(O)NH(alkyl), C(O)NH(aralkyl), C(O)NH(aryl), C(O)N(alkyl)$_2$, C(O)N(aralkyl)$_2$, C(O)N(aryl)$_2$, C(O)OH, C(O)O(alkyl), $NH_2$, NH(alkyl), NH(aralkyl), NHC(NH)$NH_2$, NHC(O)alkyl, NHC(O)aralkyl, NHC(O)aryl, NH(aryl), N(alkyl)$_2$, N(aralkyl)$_2$, N(aryl)$_2$, OH, O(alkyl), OC(O)alkyl, O(aryl), =O, SH, S(alkyl), S(aralkyl), S(aryl), S(O)alkyl, S(O)aralkyl, S(O)aryl, S(O)$_2$alkyl, S(O)$_2$aralkyl, S(O)$_2$$NH_2$, S(O)$_2$NH(alkyl), S(O)$_2$N(alkyl)$_2$, S(O)$_2$aryl, heterocyclyl, and aryl;

$R_{1D}$ is H, OH, or $OC_1$-$C_8$ alkyl, wherein the $OC_1$-$C_8$ alkyl is optionally substituted with one or more substituents independently selected from the group consisting of halo, CN, $NO_2$, C(O)alkyl, C(O)$NH_2$, C(O)NH(alkyl), C(O)NH(aralkyl), C(O)NH(aryl), C(O)N(alkyl)$_2$, C(O)N(aralkyl)$_2$, C(O)N(aryl)$_2$, C(O)OH, C(O)O(alkyl), $NH_2$, NH(alkyl), NH(aralkyl), NHC(NH)$NH_2$, NHC(O)alkyl, NHC(O)aralkyl, NHC(O)aryl, NH(aryl), N(alkyl)$_2$, N(aralkyl)$_2$, N(aryl)$_2$, OH, O(alkyl), OC(O)alkyl, O(aryl), =O, SH, S(alkyl), S(aralkyl), S(aryl), S(O)alkyl, S(O)aralkyl, S(O)aryl, S(O)$_2$alkyl, S(O)$_2$aralkyl, S(O)$_2$$NH_2$, S(O)$_2$NH(alkyl), S(O)$_2$N(alkyl)$_2$, S(O)$_2$aryl, heterocyclyl, and aryl;

$R_{1E}$ is H, OH, or $OC_1$-$C_8$ alkyl, wherein the $OC_1$-$C_8$ alkyl is optionally substituted with one or more substituents independently selected from the group consisting of halo, CN, $NO_2$, C(O)alkyl, C(O)$NH_2$, C(O)NH(alkyl), C(O)NH(aralkyl), C(O)NH(aryl), C(O)N(alkyl)$_2$, C(O)N(aralkyl)$_2$, C(O)N(aryl)$_2$, C(O)OH, C(O)O(alkyl), $NH_2$, NH(alkyl), NH(aralkyl), NHC(NH)$NH_2$, NHC(O)alkyl, NHC(O)aralkyl, NHC(O)aryl, NH(aryl), N(alkyl)$_2$, N(aralkyl)$_2$, N(aryl)$_2$, OH, O(alkyl), OC(O)alkyl, O(aryl), =O, SH, S(alkyl), S(aralkyl), S(aryl), S(O)alkyl, S(O)aralkyl, S(O)aryl, S(O)$_2$alkyl, S(O)$_2$aralkyl, S(O)$_2$$NH_2$, S(O)$_2$NH(alkyl), S(O)$_2$N(alkyl)$_2$, S(O)$_2$aryl, heterocyclyl, and aryl;

$R_{1F}$ is H, OH, or $OC_1$-$C_8$ alkyl, wherein the $OC_1$-$C_8$ alkyl is optionally substituted with one or more substituents independently selected from the group consisting of halo, CN, $NO_2$, C(O)alkyl, C(O)$NH_2$, C(O)NH(alkyl), C(O)NH(aralkyl), C(O)NH(aryl), C(O)N(alkyl)$_2$, C(O)N(aralkyl)$_2$, C(O)N(aryl)$_2$, C(O)OH, C(O)O(alkyl), $NH_2$, NH(alkyl), NH(aralkyl), NHC(NH)$NH_2$, NHC(O)alkyl, NHC(O)aralkyl, NHC(O)aryl, NH(aryl), N(alkyl)$_2$, N(aralkyl)$_2$, N(aryl)$_2$, OH, O(alkyl), OC(O)alkyl, O(aryl), =O, SH, S(alkyl), S(aralkyl), S(aryl), S(O)alkyl, S(O)aralkyl, S(O)aryl, S(O)$_2$alkyl, S(O)$_2$aralkyl, S(O)$_2$$NH_2$, S(O)$_2$NH(alkyl), S(O)$_2$N(alkyl)$_2$, S(O)$_2$aryl, heterocyclyl, and aryl;

$R_2$ is H or OH;
$R_3$ is H;
$R_4$ is H, $C_1$-$C_3$ alkyl, or $C_1$-$C_3$ fluoroalkyl;
$R_5$ is H, $C_1$-$C_6$ alkyl, or $C_1$-$C_6$ fluoroalkyl;
n is 1 or 2; and
X is acetate, acetylacetonate, bromide, chloride, citrate, ethanesulfonate, formate, fluoride, hexafluoroacetylacetonate, hexafluorophosphate, iodide, lactate, malate, maleate, methanesulfonate, nitrate, perchlorate, phosphate, salicylate, succinate, sulfate, tartrate, tetrafluoroborate, trifluoroacetate, trifluoromethanesulfonate, or p-toluenesulfonate.

2. The compound of claim 1, or a pharmaceutically acceptable salt or stereoisomer thereof, wherein:

$R_{1A}$ is H, OH, or $OCH_3$;

$R_{1B}$ is H, OH, or $OCH_3$;

$R_{1C}$ is H, OH, or $OCH_3$;

$R_{1D}$ is H, OH, or $OCH_3$;

$R_{1E}$ is H, OH, or $OCH_3$; and $R_{1F}$ is H, OH, or $OCH_3$.

3. The compound of claim 2, or a pharmaceutically acceptable salt or stereoisomer thereof, wherein:

$R_{1A}$ is H;

$R_{1B}$ is $OCH_3$;

$R_{1C}$ is H;

$R_{1D}$ is H;

$R_{1E}$ is $OCH_3$; and $R_{1F}$ is $OCH_3$.

4. The compound of claim 3, or a pharmaceutically acceptable salt or stereoisomer thereof, wherein $R_5$ is H.

5. The compound of claim 2, or a pharmaceutically acceptable salt or stereoisomer thereof, wherein:

$R_{1A}$ is $OCH_3$;

$R_{1B}$ is $OCH_3$;

$R_{1C}$ is H;

$R_{1D}$ is H;

$R_{1E}$ is $OCH_3$; and $R_{1F}$ is $OCH_3$.

6. The compound of claim 1, or a pharmaceutically acceptable salt or stereoisomer thereof, wherein $R_4$ is $CH_3$.

7. The compound of claim 1, or a pharmaceutically acceptable salt or stereoisomer thereof, wherein $R_5$ is H.

8. The compound of claim 1, or a pharmaceutically acceptable salt or stereoisomer thereof, wherein X is acetate, bromide, chloride, citrate, fluoride, formate, iodide, lactate, methanesulfonate, trifluoroacetate, trifluoromethanesulfonate, or p-toluenesulfonate.

9. The compound of claim 8, or a pharmaceutically acceptable salt or stereoisomer thereof, wherein X is bromide, chloride, fluoride, or iodide.

10. The compound of claim 9, or a pharmaceutically acceptable salt or stereoisomer thereof, wherein X is bromide.

11. The compound of claim 1, or a stereoisomer thereof, wherein the stereoisomer of Formula (I) has a structure of Formula (II), Formula (III), or Formula (IV):

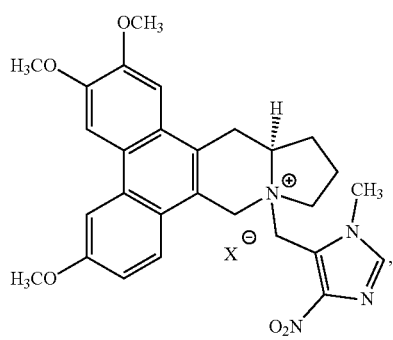

Formula (II)

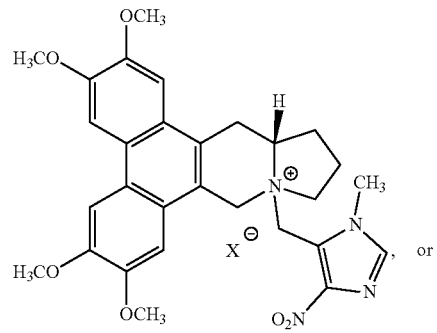

Formula (III)

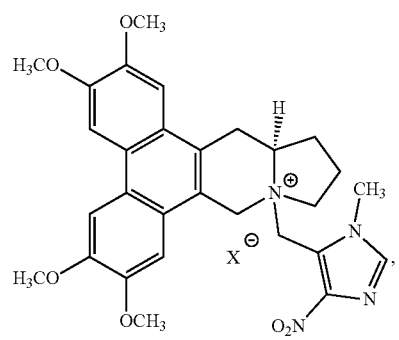

Formula (IV)

or a pharmaceutically acceptable salt thereof.

12. The compound of claim 11, or a pharmaceutically acceptable salt thereof, wherein X is acetate, bromide, chloride, citrate, fluoride, formate, iodide, lactate, methanesulfonate, trifluoroacetate, trifluoromethanesulfonate, or p-toluenesulfonate.

13. The compound of claim 12, or a pharmaceutically acceptable salt thereof, wherein X is bromide, chloride, fluoride, or iodide.

14. The compound of claim 13, or a pharmaceutically acceptable salt thereof, wherein X is bromide.

15. A pharmaceutical composition comprising a pharmaceutically acceptable carrier and/or excipient and the compound of claim 1, or a pharmaceutically acceptable salt or stereoisomer thereof.

16. The pharmaceutical composition of claim 15, wherein:
   (i) the pharmaceutically acceptable carrier is selected from the group consisting of a buffer, a fatty acid, an inorganic salt, a polymer, a surfactant, a synthetic fatty ester, and a vegetable oil, or a combination thereof; or
   (ii) the pharmaceutically acceptable excipient is selected from the group consisting of a buffer, a fatty acid, an inorganic salt, a polymer, a surfactant, a synthetic fatty ester, and a vegetable oil, or a combination thereof; or
   (iii) the pharmaceutically acceptable carrier is selected from the group consisting of a buffer, a fatty acid, an inorganic salt, a polymer, a surfactant, a synthetic fatty ester, and a vegetable oil, or a combination thereof; and the pharmaceutically acceptable excipient is selected from the group consisting of a buffer, a fatty acid, an inorganic salt, a polymer, a surfactant, a synthetic fatty ester, and a vegetable oil, or a combination thereof.

17. The pharmaceutical composition of claim 15, wherein the stereoisomer of Formula (I) has a structure of Formula (II), Formula (III), or Formula (IV):

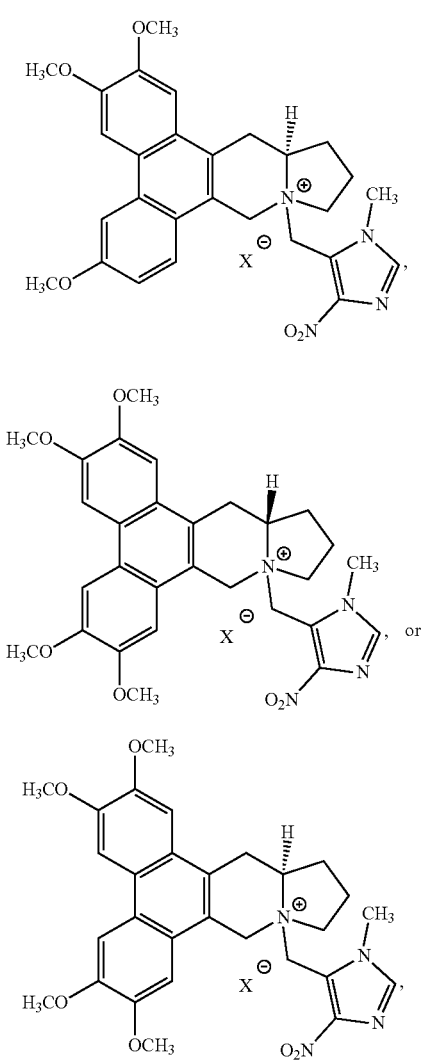

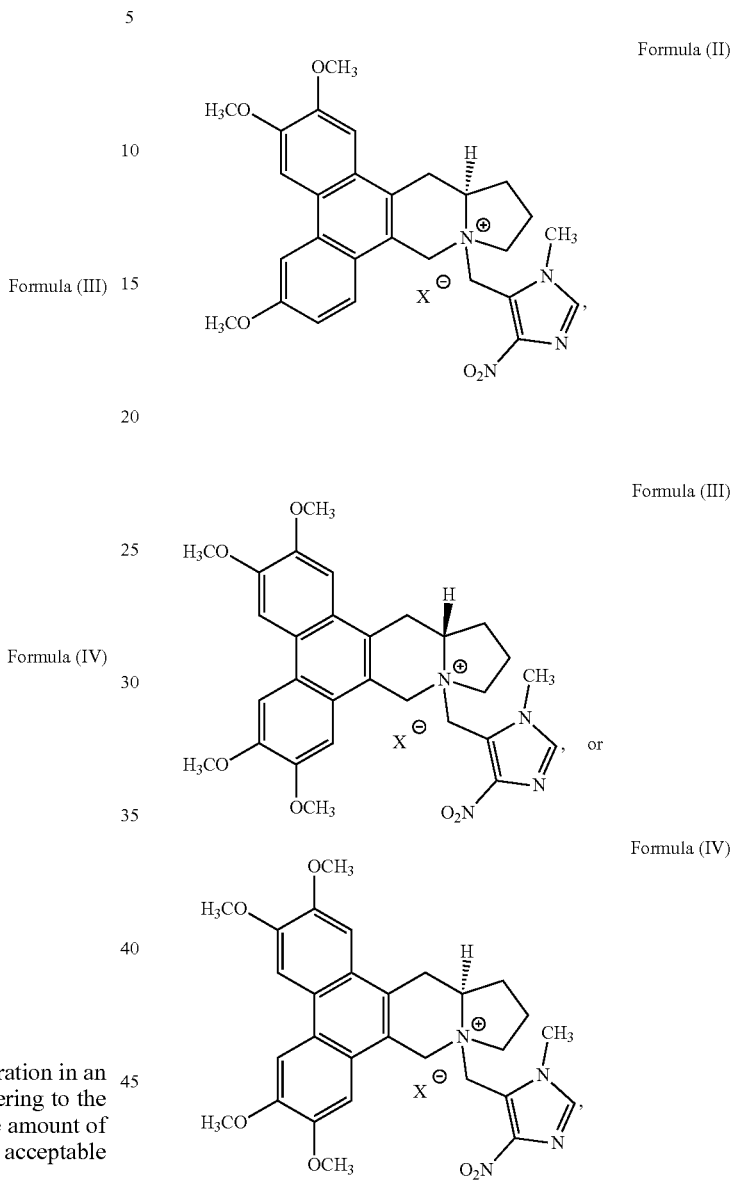

or a pharmaceutically acceptable salt thereof.

18. A method for inhibiting cancer cell proliferation in an animal, wherein the method comprises administering to the animal in need thereof a therapeutically effective amount of the compound of claim 1, or a pharmaceutically acceptable salt or stereoisomer thereof.

19. The method of claim 18, wherein the animal has a cancer selected from the group consisting of breast cancer, colon cancer, colorectal cancer, and lung cancer, or a combination thereof.

20. The method of claim 18, wherein the stereoisomer of Formula (I) has a structure of Formula (II), Formula (III), or Formula (IV):

or a pharmaceutically acceptable salt thereof.

* * * * *